US010954529B2

(12) United States Patent
Flynn et al.

(10) Patent No.: US 10,954,529 B2
(45) Date of Patent: Mar. 23, 2021

(54) MINIMAL VOLUME REPROGRAMMING OF MONONUCLEAR CELLS

(71) Applicant: Fate Therapeutics, Inc., San Diego, CA (US)

(72) Inventors: Peter Flynn, San Diego, CA (US); Bahram Valamehr, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 286 days.

(21) Appl. No.: 16/007,928

(22) Filed: Jun. 13, 2018

(65) Prior Publication Data

US 2018/0355373 A1    Dec. 13, 2018

Related U.S. Application Data

(62) Division of application No. 14/731,403, filed on Jun. 4, 2015, now Pat. No. 10,023,879.

(60) Provisional application No. 62/007,924, filed on Jun. 4, 2014.

(51) Int. Cl.
| | |
|---|---|
| C12N 5/00 | (2006.01) |
| C12N 15/85 | (2006.01) |
| A61K 35/545 | (2015.01) |
| A61K 35/51 | (2015.01) |
| A61K 35/12 | (2015.01) |

(52) U.S. Cl.
CPC ............ *C12N 15/85* (2013.01); *A61K 35/545* (2013.01); *A61K 35/51* (2013.01); *A61K 2035/124* (2013.01); *C12N 2740/16043* (2013.01); *C12N 2800/108* (2013.01); *C12N 2800/30* (2013.01); *C12N 2840/20* (2013.01)

(58) Field of Classification Search
None
See application file for complete search history.

(56) References Cited

U.S. PATENT DOCUMENTS

| | | | |
|---|---|---|---|
| 6,534,476 B2 | 3/2003 | Miyazono et al. | |
| 6,692,736 B2 | 2/2004 | Yu et al. | |
| 8,044,201 B2 | 10/2011 | Xu et al. | |
| 8,691,574 B2 | 4/2014 | Mack | |
| 9,624,470 B2* | 4/2017 | Slukvin | C12N 5/0647 |
| 2005/0119203 A1 | 6/2005 | Steinbrecher et al. | |
| 2009/0299763 A1 | 12/2009 | Sakurada | |
| 2012/0135525 A1 | 5/2012 | Brown et al. | |
| 2012/0252060 A1* | 10/2012 | Dick | C12N 5/0647 435/34 |
| 2014/0294764 A1 | 10/2014 | Yoon et al. | |
| 2020/0182870 A1* | 6/2020 | Basso-Ricci | G01N 33/582 |

FOREIGN PATENT DOCUMENTS

| | | |
|---|---|---|
| EP | 1 992 360 A1 | 11/2008 |
| WO | WO 1999/001426 A1 | 1/1999 |
| WO | WO 2002/006213 A2 | 1/2002 |
| WO | WO 2002/088346 A2 | 11/2002 |
| WO | WO 2003/077914 A1 | 9/2003 |
| WO | WO 2005/051301 A2 | 6/2005 |
| WO | WO 2007/044084 A3 | 4/2007 |
| WO | WO 2008/006583 A1 | 1/2008 |
| WO | WO 2008/094597 A2 | 8/2008 |
| WO | WO 2010/141801 A2 | 12/2010 |

OTHER PUBLICATIONS

Mian et al Blood (2013) 122 (21): 262. SF3B1 Mutant Clones From Patients With Refractory Anaemia With Ringed Sideroblasts (RARS) Originate From the Early Haematopoietic Stem Cells and Maintain Their engraftment Potential; Abstract.*
Aasen et al Efficient and rapid generation of induced pluripotent stem cells from human keratinocytes 2008; Nature biotechnology ; pp. 1276-1284.*
Chang et al., "Transforming growth factor-beta signaling in breast cancer," Front Biosci. (2007); 12:4393-4401.
Cui, "Selective inhibition of TGF-beta responsive genes by Smad-interacting peptide aptamers from FoxH1, Lef1 and CBP", Oncogene. (2005); 24(24):3864-3874.
DaCosta et al., "SB-505124 is a selective inhibitor of transforming growth factor-beta type I receptors ALK4, ALK5, and ALK7", Mol Pharmacol. (2004); 65(3):744-752.
De Gouville et al. "Inhibition of ALK5 as a new approach to treat liver fibrotic diseases", Drug News Perspect. (2006); 19(2):85-90.
Donnelly et al., "The 'cleavage' activities of foot-and-mouth disease virus 2A site-directed mutants and naturally occurring '2A-like' sequences", J Gen Virol. (2001 ); 82(Pt5): 1027-1041.
Gafni et al., "Derivation of novel human ground state naive pluripotent stem cells, " Nature, (2013); 504:282-286.
Gellibert et al., "Discovery of 4-{4-[3-(pyridin-2-yl)-1 H-pyrazol-4-yl]pyridin-2-yl}-N-(tetrahydro-2H-pyran-4-yl)benzamide (GW788388): a potent, selective, and orally active transforming growth factor-beta type I receptor inhibitor" J Med Chem. (2006); 49(7):2210-2221.
Huang et al., "Bioinformatics enrichment tools: paths toward the comprehensive functional analysis of large gene lists", Nucleic Acids Res. (2009); 37(1):1-13.
Inman et al., "SB-431542 is a potent and specific inhibitor of transforming growth factor-beta superfamily type I activin receptor-like kinase (ALK) receptors ALK4, ALK5, and ALK7", Mol Pharmacol. (2002); 62(1):65-74.
Irion et al., "Identification and targeting of the ROSA26 locus in human embryonic stem cells." Nat Biotechnol. (2007); 25(12): 1477-1482.

(Continued)

*Primary Examiner* — Maria G Leavitt
(74) *Attorney, Agent, or Firm* — Jones Day

(57) ABSTRACT

The invention provides compositions and methods for reprogramming minimal volumes of mononuclear cells. In particular aspects, the invention provides methods and compositions for reprogramming minimal volumes of umbilical cord blood obtained from cord blood segments from cryopreserved cord blood segments.

15 Claims, 21 Drawing Sheets

Specification includes a Sequence Listing.

(56) References Cited

OTHER PUBLICATIONS

Jackson et al., "Internal initiation of translation in eukaryotes: the picornavirus paradigm and beyond", RNA. (1995); 1(10):985-1000.
Jackson et al., "The novel mechanism of initiation of picornavirus RNA translation", Trends Biochem Sci. (1990); 15(12):477-483.
Kaminska et al., "TGF beta signalling and its role in tumour pathogenesis", Acta Biochim Pol. (2005); 52(2):329-337.
Lee et al., "Isolation and directed differentiation of neural crest stem cells derived from human embryonic stem cells", Nat. Biotechnol. (2007); 25:1468-1475.
Rao et al., "Concise review: cord blood banking, transplantation and induced pluripotent stem cell: success and opportunities," Stem Cells, (2012); 30:55-60.
Rosskopf et al., "Quality controls of cryopreserved haematopoietic progenitor cells (peripheral blood, cord blood, bone marrow)," Vox Sanguinis, (2011); 101:255-275.
Ryan et al., "Virus-encoded proteinases of the picornavirus supergroup", J Gen Virol. (1997); 78 (Pt 4):699-723.
Shimanuki et al., "Modulation of the functional binding sites for TGF-beta on the type II receptor leads to suppression of TGF-beta signaling", Oncogene (2007); 26(23):3311-20.
Spellman et al., "Guidelines for the development and validation of new potency assays for the evaluation of umbilical cord blood," Cytotherapy, (2011); 13(7):848-855.
Suzuki et al., "A novel small-molecule inhibitor of transforming growth factor beta type I receptor kinase (SM16) inhibits murine mesothelioma tumor growth in vivo and prevents tumor recurrence after surgical resection", Cancer Res. (2007); 67(5):2351-2359.
Szymczak et al., "Correction of multi-gene deficiency in vivo using a single 'self-cleaving' 2A peptide-based retroviral vector", Nat Biotechnol. (2004); 22(5):589-594.
Tojo et al. "The ALK-5 inhibitor A-83-01 inhibits Smad signaling and epithelial-to-mesenchymal transition by transforming growth factor-beta", Cancer Sci. (2005); 96(11):791-800.
Valamehr et al., "A novel platform to enable the high-throughput derivation and characterization of feeder-free human iPSCs" Sci. Reports, 2:213 (2012).
Valamehr et al., "Platform for Induction and Maintenance of Transgene-free hiPSCs Resembling Ground State Pluripotent Stem Cells" Stem Cell Reports (2014) 2:366-373.
Wrzesinski et al., "Transforming growth factor-beta and the immune response: implications for anticancer therapy", Clin Cancer Res. (2007); 13(18 Pt 1):5262-5270.
Yu et al., "Human Induced Pluripotent Stem Cells Free of Vector and Transgene Sequences" Science, (2009); 324(5928):797-801.
Zhao et al., "Inhibition of transforming growth factor-beta1-induced signaling and epithelial-to-mesenchymal transition by the Smad-binding peptide aptamer Trx-SARA", Mol Biol Cell. (2006); 17(9):3819-3831.

* cited by examiner

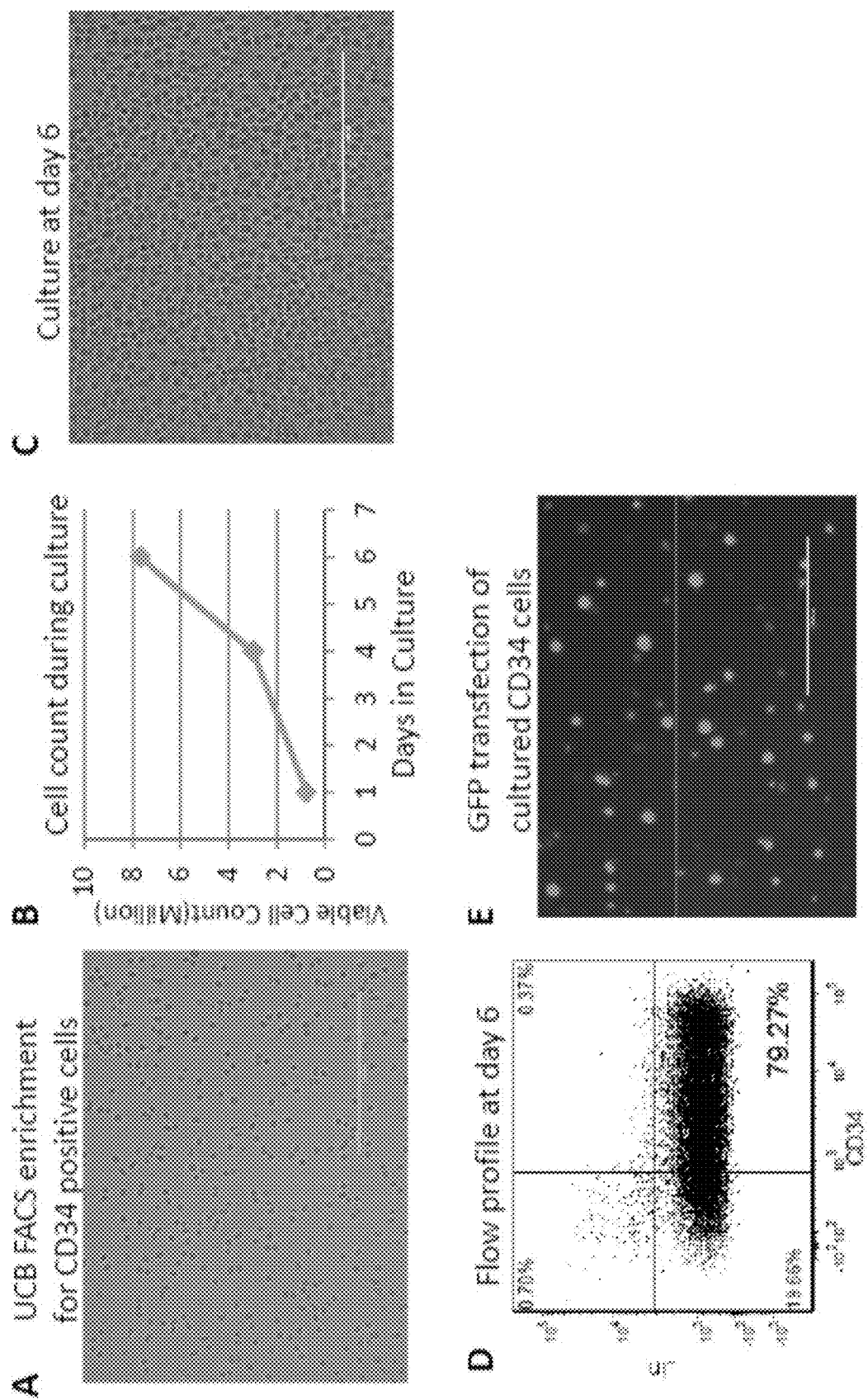
FIGS. 2A-E

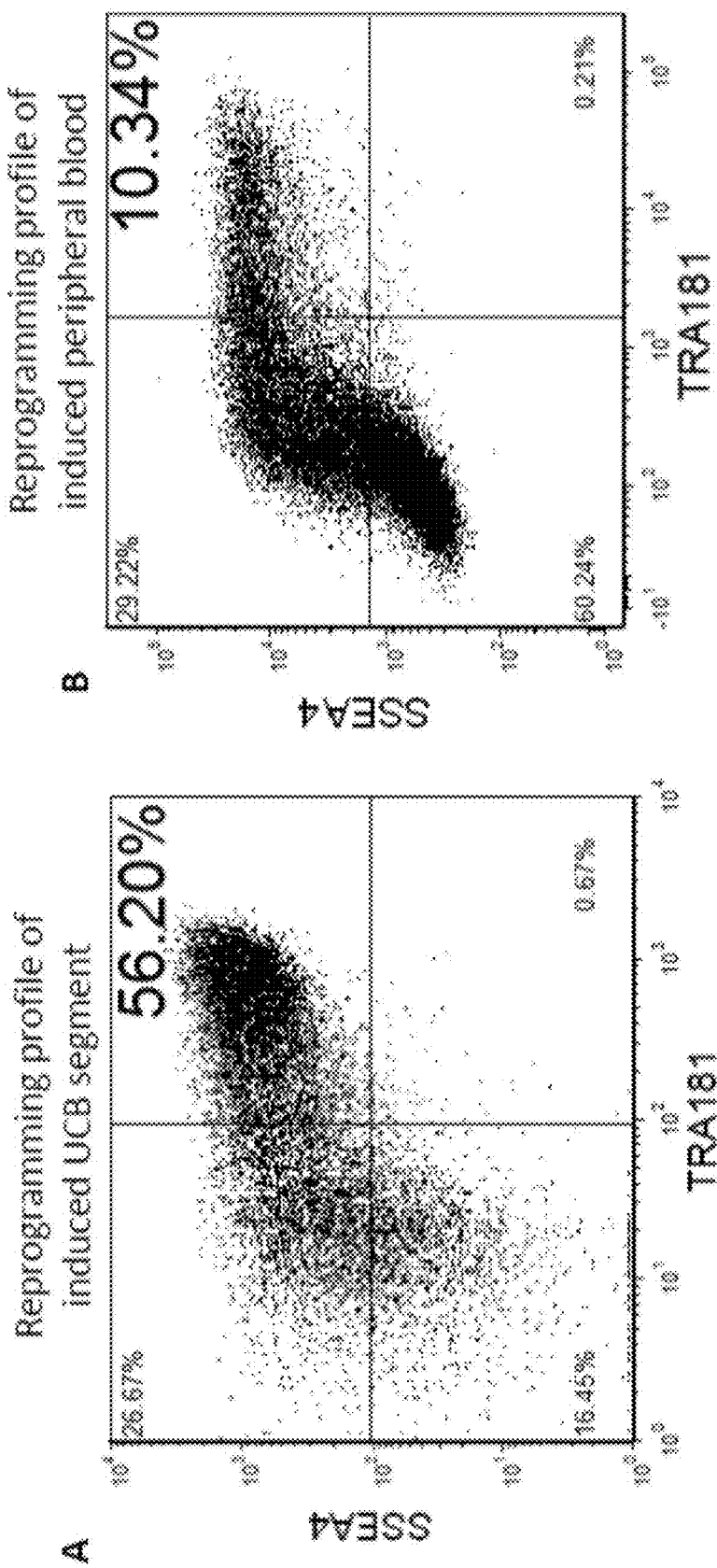
FIGS. 3A-B

FIG. 6A CONT'D

MINIMAL VOLUME REPROGRAMMING OF MONONUCLEAR CELLS

CROSS-REFERENCE TO RELATED APPLICATIONS

This application is a division of U.S. application Ser. No. 14/731,403, filed Jun. 4, 2015, now U.S. Pat. No. 10,023,879, which claims the benefit under 35 U.S.C. § 119(e) of U.S. Provisional Application No. 62/007,924, filed Jun. 4, 2014, both of which are incorporated by reference in their entirety.

SUBMISSION OF SEQUENCE LISTING ON ASCII TEXT FILE

This application incorporates by reference the Computer Readable Form (CRF) of a Sequence Listing in ASCII text format submitted via EFS-Web. The Sequence Listing text file submitted via EFS-Web, entitled 13601-211-999_Substitute_SEQ_LISTING_2021-01-13, was created on Jan. 13, 2021, and is 4,438 bytes in size.

BACKGROUND

Technical Field

The invention generally relates to compositions and methods for reprogramming non-pluripotent cells. More particularly, the invention relates to reprogramming mononuclear cells from low volume samples of blood.

Description of Related Art

Through their ability to self-renew and differentiate into any somatic cell type, induced pluripotent stem cells (iPSCs) have remarkable, but as yet untapped, therapeutic potential. Blood provides an attractive source of somatic cells for reprogramming as it is available in relatively large volumes and is easy to collect. However, blood, like other sources of explant-derived somatic cells for reprogramming, has some limitations in therapeutic applications since it must be HLA-typed and screened for pathogens before reprogrammed cells can be administered to a subject. What is needed in the art therefore is a readily accessible source of mononuclear cells for reprogramming that has been screened for HLA compatibility, pathogens and genetic abnormalities in the donor.

SUMMARY OF THE INVENTION

The invention overcomes the limitations in the art by providing compositions and methods for using cord blood segments from umbilical cord blood (UCB) units as a source of somatic cells for cellular reprogramming. UCB represents an attractive starting material for the generation of allogeneic human induced pluripotent stem cells (hiPSCs) for therapeutic applications since it is an accessible, banked, tested, HLA-typed source of cells with established donor consent and reduced chance of age-related genetic mutations. Because UCB units that have been screened in this manner are often cryopreserved for later use by an HLA-compatible recipient, the invention's use of cord blood segments prevents the need to thaw UCB units thereby preserving the UCB unit for other applications such as transplantation therapy or further reprogramming.

Cord blood segments are segments of tubing that form an integral part of a cord blood bag and contain a portion of UCB from the cord blood unit. Cord blood segments are formed when the tubing is sealed in sections to provide small volumes or "segments" of UCB. Currently, cord blood segments of cryopreserved UCB are only used for confirmatory and diagnostic testing purposes. The minimal volume in these frozen segments represents a major challenge for culturing and further processing since the number of mono-nucleated cells present in such samples is relatively small. This difficulty is compounded in cellular reprogramming contexts since cellular reprogramming itself is an inefficient process, especially when attempting non-integrative methods and without the use of oncogenes such as KLF4 and MYC.

The invention overcomes these difficulties by providing methods and compositions for reprogramming mononuclear cells from minimal volumes of screened blood to derive human induced pluripotent stem cells that are suitable for transplantation.

It is therefore an object of the invention to provide a method of producing induced pluripotent stem cells (iPSC) from blood comprising providing a minimal volume of blood comprising mononuclear cells, and reprogramming the mononuclear cells to iPSC by introducing to the mononuclear cells at least one polynucleotide encoding least one reprogramming factor polypeptide or introducing to the mononuclear cells at least one reprogramming factor polypeptide.

A further object of the invention is to provide a method of producing iPSC from umbilical cord blood comprising: providing a sample of cryopreserved umbilical cord blood comprising mononuclear cells, wherein the sample is between about 1 mL and about 10 µL in volume; introducing to the mononuclear cells a composition comprising (i) at least one polynucleotide encoding at least one reprogramming factor polypeptide, or (ii) at least one reprogramming factor polypeptide; contacting the mononuclear cells with at least one of a GSK3 inhibitor, a MEK inhibitor, a ROCK inhibitor, and a TGFβR inhibitor; and culturing the contacted mononuclear cells in a culture medium comprising a GSK3 inhibitor, a MEK inhibitor, and a ROCK inhibitor, but not a TGFβR inhibitor.

In some aspects of the invention, the cryopreserved umbilical cord blood is obtained from a segment from an umbilical cord unit.

A further object of the invention is to provide a composition comprising (i) between about 1 mL and about 10 µL of umbilical cord blood or peripheral blood, and (ii) at least one exogenous polynucleotide encoding at least one reprogramming factor polypeptide, or at least one exogenous reprogramming factor polypeptide.

In some aspects of the invention, the composition comprises at least one of a GSK3 inhibitor, a MEK inhibitor, a ROCK inhibitor, and a TGFβR inhibitor.

A further objective of the invention is to provide a composition comprising between about 100 and $1 \times 10^4$ mononuclear cells, and (i) at least one exogenous polynucleotide encoding at least one reprogramming factor polypeptide, or (ii) at least one exogenous reprogramming factor polypeptide.

In some aspects of the invention, the composition comprises less than about $1 \times 10^4$ mononuclear cells.

In some aspects of the invention, the composition comprises at least one of a GSK3 inhibitor, a MEK inhibitor, a ROCK inhibitor, and a TGFβR inhibitor.

A further object of the invention is to provide a kit for producing iPSC wherein the kit comprises a minimal volume of blood, and (i) at least one polynucleotide encoding at least one reprogramming factor polypeptide, or (ii) at least one reprogramming factor polypeptide.

In some aspects of the invention, the blood comprises a segment from an umbilical cord unit.

In some aspects of the invention, the kit comprises at least one of a GSK3 inhibitor, a MEK inhibitor, a ROCK inhibitor, and a TGFβR inhibitor.

A further object of the invention is to provide a kit for producing iPSC wherein the kit comprises between about 100 and 1×10$^4$ mononuclear cells, and (i) at least one polynucleotide encoding at least one reprogramming factor polypeptide, or (ii) at least one reprogramming factor polypeptide.

In some aspects of the invention, the kit comprises less than about 1×10$^4$ mononuclear cells.

In some aspects of the invention, the kit comprises at least one of a GSK3 inhibitor, a MEK inhibitor, a ROCK inhibitor, and a TGFβR inhibitor.

BRIEF DESCRIPTION OF THE DRAWINGS

FIGS. 2A-2E. CD34 enrichment and culture post segment harvest. FIG. 2A) CD34 positive cells derived from segments by FACS transferred to culture for expansion. FIG. 2B) Sorted cells efficiently expand in culture conditions. FIG. 2C) Appearance and FIG. 2D) flow profile of cultured cells. A majority of the cells retained their stem cell property as demonstrated by large population subset expressing CD34. FIG. 2E) Cultured cells are readily transfected as demonstrated with GFP.

FIGS. 3A and 3B. Reprogramming of starting blood cells. Flow cytometry profile of reprogramming pools of FIG. 3A) cord blood segment of FIG. 3B) peripheral blood after 2 weeks post induction with a non-integrating method expressing OCT4 and SOX2.

FIG. 4A) Flow cytometry sorting of episomal induced reprogramming of various starting cell lines reprogrammed in feeder cell-free culture directly added to 96-well plate. FIG. 4B) qRT-PCR for NANOG expression for each well of a SSEA4/TRA181/CD30 direct sorted (FACS) 96-well plate. FIG. 4C) Pluripotency markers detected by immunofluorescence. FIG. 4D) PCR analysis for episomal DNA derived from various hiPSC clones. Lanes 1-6, derived clonal hiPSC lines; Lane 7, a line maintaining episomal constructs used a positive control; Lane 8, untransfected starting line; Lane 9, hiPSC generated using lentiviral constructs (to serve as a control against cross contamination); Lane 10, episomal vector used as positive control. Input of 100 ng genomic DNA and 30 PCR cycles were used for all sets. FIG. 4E) Flow cytometry profile for selected hiPSC clones from various parental lines. Upper row profiles SSEA4/TRA181 surface expression. Bottom row profiles OCT4/NANOG intracellular expression.

FIG. 5A) Flow cytometry profile and cytogenetic analysis of long-term passaged hiPSC clones in feeder-free and single cell enzymatically passaged culture. FIG. 5B) Copy number variation as assessed by array comparative genomic hybridization and single nucleotide polymorphism. FIG. 5C) Embryoid body formation and differentiation. Immunocytochemistry conducted 28 days post differentiation: Ectoderm, Tuj 1; Mesoderm, alpha smooth muscle actin (aSMA); Endoderm, AFP. FIG. 5D) Histological sections of teratoma derived from hiPSCs. Black arrows, endoderm; white arrows, ectoderm; gray arrows, mesoderm.

FIG. 6A) Heatmap derived from a Fluidigm dynamic array depicting relative gene expression levels of pluripotency and differentiation genes of conventionally grown cells versus cells grown in FMM. FIG. 6B) Hierarchical clustering on the 339 probe sets using a complete linkage method based on Euclidean distance measurements. FIG. 6C) Representative images of HEK27me3 in a hiPSC clone maintained in FMM media or adapted to conventional culture for 5 passages.

DEFINITIONS

Figure 1:
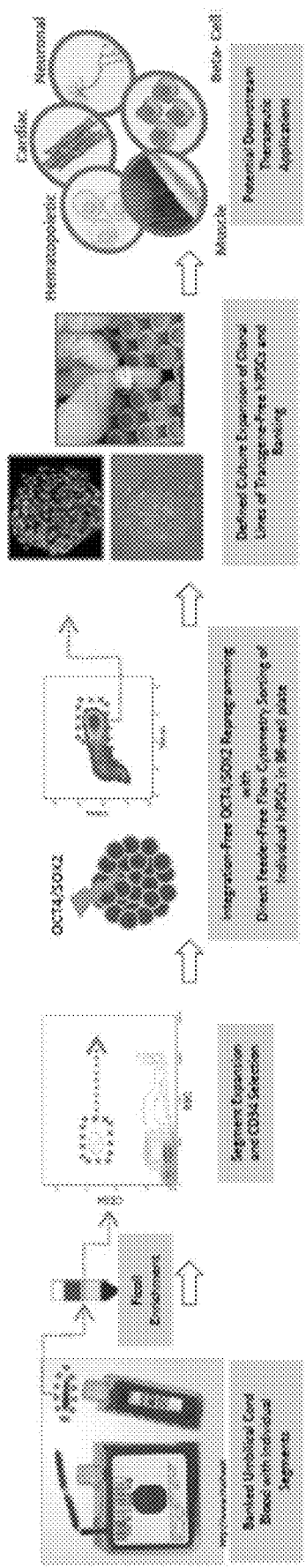
FIG. 1. Schematic representation of an embodiment for producing human induced pluripotent stem cells (hiPSCs) from UCB segments and subsequent, characterization and banking. A segment of banked umbilical cord blood, such as 100 μL in volume, is Ficoll treated for mononuclear cells and expanded for 1-2 weeks in hematopoietic stem cell expansion medium. The culture is further enriched for stem and progenitor population and induced to reprogram using, for example, a non-integrative strategy to express OCT4 and SOX2 in defined culture. After 2 weeks in culture, reprogrammed cells expressing SSEA4/TRA181/CD30 are directly sorted into 96-well plates. Individual hiPSC colonies are then expanded in defined culture and selected clones are optionally banked as HLA-matched allogeneic lines for potential therapeutic use.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "appreciable" refers to a range of quantity, level, value, number, frequency, percentage, dimension, size, amount, weight or length or an event that is readily detectable by one or more standard methods. The terms "not-appreciable" and "not appreciable" and equivalents refer to a range of quantity, level, value, number, frequency, percentage, dimension, size, amount, weight or length or an event that is not readily detectable or undetectable by standard methods. In one embodiment, an event is not appreciable if it occurs less than 5%, 4%, 3%, 2%, 1%, 0.1%, 0.01%, 0.001% or less of the time.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%, or any intervening range thereof.

As used herein, the term "mononuclear cell" refers to a cell found in blood that has a single, round nucleus.

As used herein, the term "pluripotent" refers to the ability of a cell to form all lineages of the body or soma (i.e., the embryo proper). For example, an embryonic stem cell is a type of pluripotent stem cell that is able to form cells from each of the three germs layers: the ectoderm, the mesoderm, and the endoderm. Pluripotency can be determined, in part, by assessing pluripotency characteristics of the cells. Pluripotency characteristics include, but are not limited to: (i) pluripotent stem cell morphology; (ii) the potential for unlimited self renewal (iii) expression of pluripotent stem cell markers including, but not limited to SSEA1 (mouse only), SSEA3/4; SSEA5, TRA1-60/81; TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm) (v) teratoma formation consisting of the three somatic lineages; and (vi) formation of embryoid bodies consisting of cells from the three somatic lineages.

As used herein, the term "non-pluripotent cell" refers to any cell that does not possess full pluripotency, such as incompletely or partially pluripotent stem cells, multipotent cells, oligopotent cells, unipotent cells (e.g. progenitor cells), and terminally differentiated cells.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "introducing" refers to a process that comprises contacting a cell with a polynucleotide, polypeptide, or small molecule. An introducing step may also comprise microinjection of polynucleotides or polypeptides into the cell, use of liposomes to deliver polynucleotides or polypeptides into the cell, or fusion of polynucleotides or polypeptides to cell permeable moieties to introduce them into the cell.

As used herein, the term "reprogramming efficiency" refers to the number of cells in a sample that are successfully reprogrammed to pluripotentcy relative to the total number of cells in the sample. Reprogramming efficiency may be measured as a function of pluripotency markers. Such pluripotency markers include, but are not limited to, the expression of pluripotency marker proteins and mRNA, pluripotent cell morphology and colony formation. For example, a reprogramming efficiency of 5% indicates that 5% of the cells in a sample of cells co-expresses SSEA4 and TRA-181/160.

As used herein, "culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

As used herein, "cultivate" refers to the sustaining, propagating (growing) and/or differentiating of cells outside of tissue or the body, for example in a sterile plastic (or coated plastic) cell culture dish or flask. "Cultivation" may utilize a culture medium as a source of nutrients, hormones and/or other factors helpful to propagate and/or sustain the cells.

As used herein, the terms "enrich," "enriching," "select" and "selecting" are used interchangeably herein to refer to increasing the amount of a specified component in a composition, such as a composition of cells, and "enriched", when used to describe a composition of cells such as a cell population, refers to a population of cells having an increased amount proportionally of a specified component as compared to the proportion of such component in the population of cells prior to being enriched. For example, a composition such as a population of cells may be enriched with respect to a target cell type (i.e., cells having specified characteristics), thus having an increased proportion or percent of the target cell type as compared to the proportion of the target cells present in the population of cells before being enriched. A population of cells may be enriched for a target cell type by cell selection and sorting methods known in the art. In some embodiments, a population of cells is enriched by a sorting or selection process as described in the examples herein. In a particular embodiment, a method that enriches for a target cell population enriches the cell population with respect to the target cell population by at least about 20%, meaning that the enriched cell population comprises proportionately about 20% more of the target cell type than in the population before the population was enriched. In one embodiment, a method that enriches for a target cell population enriches the cell population with respect to the target cell population proportionately by at least about 30+%, 40+%, 50+%, 60+%, 70+%, 80%, 85%, 90%, 95%, 97%, 98% or 99%, or at least about 98%, or in particular embodiments, about 99%.

"Isolate" or "isolating" refers to separating and collecting a composition or material from its natural environment, such as the separating of individual cell or cell cultures from tissue or the body. In one aspect, a population or composition of cells is substantially free of cells and materials with which it can be associated in nature. "Isolated" or "purified" or "substantially pure", with respect to a target population of cells, refers to a population of cells that is at least about 50%, at least about 75%, at least about 85%, at least about 90%, and in particular embodiments, at least about 95% pure, with respect to the target cells making up a total cell population. Purity of a population or composition of cells can be assessed by appropriate methods that are well known in the art. For example, a substantially pure population of pluripotent cells refers to a population of cells that is at least about 50%, at least about 75%, at least about 85%, at least about 90%, and in particular embodiments at least about 95%, and in certain embodiments about 98% pure, with respect to pluripotent cells making up the total cell population. The term "essentially pure" is used interchangeably herein with "substantially pure".

Two types of pluripotency have previously been described: the "primed" or "metastable" state of pluripotency akin to the epiblast stem cells (EpiSC) of the late blastocyst and the "Naïve" or "Ground" state of pluripotency akin to the inner cell mass of the early/preimplantation blastocyst. While both pluripotent states exhibit the characteristics as described above, the naïve or ground state further exhibits; (i) preinactivation or reactivation of the X-chromosome in female cells (ii) improved clonality and survival during single-cell culturing (iii) global reduction in DNA methylation, (iv) reduction of H3K27me3 repressive chromatin mark deposition on developmental regulatory gene promoters, and (v) reduced expression of differentiation markers relative to primed state pluripotent cells. Standard methodologies of cellular reprogramming in which exogenous pluripotency genes are introduced to a somatic cell, expressed and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the phrase "human leukocyte antigens matched," or "HLA-matched," refers to the immunological compatibility of the human leukocyte antigens between a donor of a tissue or cell sample, and the recipient of the tissue or cell sample.

As used herein, the term "cord blood segment," or "segment," refers to a compartment on a cord blood freezing bag that is typically used for producing detachable aliquots of cord blood for confirmatory testing. The terms "cord blood segment" and "segment" may also refer to the blood (or other material) contained within such compartment.

"Primary culture" refers to cells, tissue and/or culture where the isolated cells are placed in a first culture vessel with culture medium. The cells, tissue and/or culture may be sustained and/or may proliferate, however, as long as the cells, tissue and/or culture remain in the first vessel the cells, tissue and/or culture are referred to as the primary culture.

As used herein, the term "non-integrative reprogramming" refers to a method of reprogramming a non-pluripotent stem cell by introducing one or more reprogramming factors by any means that does not result in an exogenous polynucleotide becoming part of or integrated into the reprogrammed cell genome. Non-integrative reprogramming may also be referred to as "footprint-free reprogramming."

As used herein, the term "minimal volume" refers to a volume that is about, or less than, 1 ml. Some non-limiting embodiments of a minimal volume include, but are not limited to, about, or less than, 900 µl, 800 µl, 700 µl, 600 µl, 500 µl, 400 µl, 300 µl, 200 µl, 100 µl or 50 µl, as well as about, or less than, any volume intervening these volumes.

As used herein, the term "cryopreservation" refers to a process of cooling and storing cells, tissues, or organs at low temperatures to maintain their viability. For example, cryopreservation includes the cooling and storing of cells, tissues, or organs at or below freezing (i.e. 0° C.).

As used herein, the term "cryopreserved" refers to a material that has been subjected to cryopreservation.

As used herein, the term "single cell culture" refers to the culture and expansion of cells from non-aggregated, individual cells.

As used herein, the term "reprogrammed" refers to a somatic cell that has been reprogrammed to an induced pluripotent stem cell (iPSC).

As used herein, a "feeder-free" (FF) environment refers to an environment such as a cell culture or culture media essentially free of feeder cells and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium.

The terms "small molecule reprogramming agent" or "small molecule reprogramming compound" are used interchangeably herein and refer to small molecules that can increase developmental potency of a cell, either alone or in combination with other pluripotency factors. A "small molecule" refers to an agent that has a molecular weight of less than about 5 kD, less than about 4 kD, less than about 3 kD, less than about 2 kD, less than about 1 kD, or less than about 0.5 kD. Small molecules include, but are not limited to: nucleic acids, peptidomimetics, peptoids, carbohydrates, lipids or other organic or inorganic molecules. Libraries of chemical and/or biological mixtures, such as fungal, bacterial, or algal extracts, are known in the art and can be used as a source of small molecules in certain embodiments. In particular embodiments, the small molecule reprogramming agent used herein has a molecular weight of less than 10,000 daltons, for example, less than 8,000, 6,000, 4,000, 2,000 daltons, e.g., between 50-1,500, 500-1,500, 200-2,000, 500-5,000 daltons.

DETAILED DESCRIPTION

The present invention relates to methods and compositions for reprogramming mononuclear cells to induced pluripotent stem cells (iPSC) using minimal volumes of blood. Mononuclear cells capable of being reprogrammed form a small portion of the cells found in the blood. Thus, minimal volumes of blood provide few cells capable of being reprogrammed. The difficulty of reprogramming cells from minimal volumes of blood is further complicated by the relative inefficiency of known reprogramming methods which typically fail to reprogram a large number of cells in a given sample. Despite these challenges, the inventors surprisingly discovered that efficient reprogramming of mononuclear cells from minimal volumes of blood can be accomplished through the use of the methods and compositions herein.

The development and use of UCB cryostorage technology and cord blood segments represents a unique opportunity to reprogram cells of a predefined identity. By reprogramming minimal volumes of UCB found in cord blood segments, the invention provides prequalified cGMP-grade Human Leukocyte Antigens (HLA)-matched hiPSCs that can be banked and applied to any number of downstream differentiated allogeneic cell therapies. Such allogeneic hiPSC banks could be created with appropriate HLA diversity to enable application to the broadest patient population. Accordingly, UCB represents an attractive starting material source for the generation of allogeneic hiPSCs for therapeutic applications: they are an accessible, banked, tested, HLA-typed source of cells with established donor consent and reduced chance of age-related genetic mutations. The development and use of UCB cryostorage technology that includes sampling segments represents a unique opportunity to reprogram cells of a predefined identity without compromising the main UCB unit itself. UCB unit sampling segments typically consist of 100 µL volume with minimal number of mononuclear cells. In some aspects, the invention provides a reprogramming platform comprising a multistage process for UCB segment CD34$^+$ cell selection, expansion, non-integrating cellular reprogramming and scalable iPSC culture. The platform can comprise stage-specific media formulations containing unique small molecule cocktails for enhancing the expansion and reprogramming of mononuclear cells and the maintenance and banking of reprogrammed mononuclear cells (e.g. iPSC). iPSCs reprogrammed according to the methods and compositions of the invention can be free of transgene, readily cultured and expandable as single cells while maintaining a homogenous and genomically stable pluripotent population. iPSCs generated or maintained in the media compositions described herein can exhibit properties associated with the ground state of pluripotency including enhanced cell viability and stability in single cell applications.

Mononuclear cells for use with the invention may be obtained from any source that provides cells capable of being reprogrammed using the methods and compositions disclosed herein. Mononuclear cells may be obtained from blood, a primary culture of mononuclear cells, or a clonal cell line, for example. Suitable sources of blood include, but are not limited to, peripheral blood, placental blood and umbilical cord blood (UCB). Peripheral blood may be mobilized according to methods known in the art. Blood for use with the invention may be fresh or cryopreserved and may be human or non-human in origin. Non-human sources of blood, include, but are not limited to, non-human primate, mouse, rat, horse, pig, bovine and avian sources. In a specific, non-limiting embodiment of the invention, mononuclear cells from human cord blood are reprogrammed to iPSC. In another specific, non-limiting embodiment of the invention, mononuclear cells from a segment of cryopreserved human cord blood that is suitable for transplantation (e.g. screened for pathogens and HLA typed for matching with an intended recipient) is used for reprogramming mononuclear cells to iPSC. Thus, mononuclear cells reprogrammed from UCB can be used in cell therapy.

In some aspects of the invention, mononuclear cells for reprogramming are obtained from the segment of a UCB cryopreservation bag containing UCB, such as a cord blood unit intended for transplantation. UCB blood may be fresh or cryoperserved. In embodiments where the segment of UCB is obtained from a cryopreserved cord blood unit, the invention can provide a sufficient number of mononuclear cells for reprogramming, while maintaining the remainder of the cord blood unit in a cryopreserved state. Thus, the invention allows the mononuclear cells from a cryopreserved cord blood unit to be evaluated for their reprogramming and therapeutic potential, while maintaining the cord blood unit as a source of mononuclear cells for further reprogramming, testing, research and/or therapeutic applications.

Mononuclear cells may be derived from any source that can provide cells capable of being reprogrammed according to the methods and compositions disclosed herein, and may be heterogeneous or homogeneous with respect to cell types or state of pluripotency. Mononuclear cells may be a "mixed" population of cells comprising cells of varying degrees of developmental potency. Suitable mononuclear cells for reprogramming according to the invention include, but are not limited to, non-pluripotent cells, incompletely or partially pluripotent stem cells, multipotent cells, oligopotent cells, unipotent cells, terminally differentiated cells, or a mixed population of cells comprising any combination of the foregoing. Some non-limiting examples of mononuclear cells that may be reprogrammed as disclosed herein include, but are not limited to, hematopoetic stem and progenitor cells (e.g. CD34+ cells), CD45+/CD34+/Lineage− cells, CD45+/Lineage− cells, myeloid progenitor cells, lymphoid progenitor cells, mast cells, monocytes, NK cells, lymphocytes, cytotoxic T cells, helper T cells, regulatory T cells, natural killer T cells, memory T cells, B-cells (e.g. plasma B cells, memory B cells, B-1 cells and B-2 cells), neutrophils, macrophages, basophils, dendritic cells, eosinophils or a combination thereof.

One aspect of the invention relates to compositions for reprogramming mononuclear cells to iPSC. In some embodiments, mononuclear cells are reprogrammed by introducing to the mononuclear cells polynucleotides that encode one or more of the polypeptides OCT4, SOX2, NANOG, KLF4, LIN28, c-MYC, SV40LT, hTERT, SALL4, GLIS, ESRRB, DPPA2, ECAT1, SOX1, SOX3, KLF2, KLF5, 1-MYC, n-MYC, LRH1, UTF1, TBX3, TFCP2L1, SOCS3, STAT3, and TEX10. In one non-limiting embodiment of the invention, mononuclear cells are reprogrammed with one or more polynucleotides encoding OCT4, SOX2, SV40LT, but not KLF4 or c-Myc. In another non-limiting embodiment, mononuclear cells are reprogrammed by introducing polynucleotides encoding OCT4, SOX2 and SV40LT, but not c-MYC or KLF4. In another non-limiting embodiment, mononuclear cells are reprogrammed by introducing OCT4, SOX2 and SV40LT, but not c-MYC or KLF4. In another non-limiting embodiment, mononuclear cells are reprogrammed by introducing polynucleotides encoding TBX3, TFCP2L1, and SOCS3, but not c-MYC or KLF4. In another non-limiting embodiment, mononuclear cells are reprogrammed by introducing polynucleotides encoding OCT4, SOX2, c-MYC and KLF4. Reprogramming may be accomplished by introducing one or more copies of the reprogramming factors disclosed herein. The invention further contemplates introducing the above reprogramming factors to cells in the form of a polypeptide and/or mRNA.

In particular embodiments, one or more polynucleotides encoding 1, 2, 3, 4, 5 or more copies of one or more of the reprogramming factors selected from the group consisting of: OCT4, SOX2, NANOG, KLF4, LIN28, c-MYC, SV40LT, hTERT, SALL4, GLIS, ESRRB, DPPA2, ECAT1, SOX1, SOX3, KLF2, KLF5, 1-MYC, n-MYC, LRH1, UTF1, TBX3, TFCP2L1, SOCS3, STAT3, and TEX10 may be introduced into a mononuclear cell to reprogram the cell. The copy number of each reprogramming factor introduced into the cell may be the same or different in any combination suitable to achieve reprogramming.

In particular embodiments, one or more polynucleotides may be arranged in any suitable order within a larger polynucleotide, such as a vector (e.g. polycistronic vector). In some embodiments, the vector is an episomal vector.

The polynucleotides contemplated herein, regardless of the length of the coding sequence itself, may be combined with other DNA sequences, such as expression control sequences, promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated and/or expressed using any of a variety of well established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, Sendai virus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Illustrative ubiquitous expression control sequences suitable for use in particular embodiments of the invention include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression can also be achieved by using a site specific DNA recombinase. According to certain embodiments of the invention, polynucleotides comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

In particular embodiments, polynucleotides contemplated herein, include one or more polynucleotides that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides. As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990).

The polynucleotides contemplated herein may be engineered to provide a self-cleaving peptide through the incorporate of a protease cleavage site. Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase.

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

One aspect of the invention relates to preparing a minimal volume of blood for reprogramming the mononuclear cells contained therein. In one non-limiting embodiment of the invention, reprogramming factors are introduced directly to the minimal volume of blood. The reprogrammed mononuclear cells (e.g. iPSC) thus obtained may then be serially expanded or selected according to methods known in the art, such as FACS. In another non-limiting embodiment of the invention, the minimal volume of blood is subjected to methods for purifying the mononuclear cells, such as the removal of erythrocytes by a Ficoll gradient. The purified mononuclear cells may then be (i) reprogrammed and then expanded and optionally subjected to selection methods (e.g. FACS) to obtain a either homogenous population of iPSC or fully clonal iPSC population, (ii) expanded and subsequently reprogrammed and then optionally subjected to selection methods to obtain a homogenous population of iPSC or fully clonal iPSC population, (iii) subjected to selection methods to obtain a specific cell population (e.g. CD34+ cells) and then reprogrammed, or (iv) subjected to selection methods to obtain a specific cell population (e.g. CD34+ cells) and subsequently expanded and then reprogrammed. In some aspects of the invention, mononuclear cells are reprogrammed to a pluripotent state. Reprogrammed cells may be cultured under conditions sufficient as disclosed herein to provide ground state pluripotent cells.

In embodiments of the invention, a specific population of mononuclear cells from the minimal volume of blood is selected for reprogramming using methods known in the art, including, but not limited to, fluorescent activated cell sorting (FACS) and magnetic assisted cell sorting (MACS) (e.g. immuno-magnetic bead selection). Non-limiting examples of mononuclear cells suitable for practicing the invention include, but are not limited to, CD45+/CD34+/Lineage-cells, CD45+/Lineage− cells, hematopoetic stem and progenitor cells (e.g. CD34+ cells), myeloid progenitor cells, lymphoid progenitor cells, mast cells, monocytes, lymphocytes, cytotoxic T cells, helper T cells, regulatory T cells, natural killer T cells, memory T cells, B cells (e.g. plasma B cells, memory B cells, B-1 cells and B-2 cells), neutrophils, macrophages, basophils, dendritic cells and eosinophils.

In some embodiments of the invention, mononuclear cells are reprogrammed by non-integrative reprogramming. Suitable methods of non-integrative reprogramming for use with the invention include, but are not limited to, non-integrating lentivirus, Sendai virus, episomal reprogramming, or, introducing mRNA or naked DNA by chemical or electroporation methodologies or applying reprogramming factors as fusion proteins with protein transduction domains.

In some embodiments, the invention provides methods for culturing and expanding mononuclear cells from a minimal volume blood (e.g. umbilical cord blood, placental blood or peripheral blood). As with other embodiments of the invention, blood for use with the invention may be obtained from human or non-human sources, such non-human sources including, but not limited to non-human primate, mouse, rat, horse, pig, bovine and avian. Suitable mononuclear cells for culturing and expanding as disclosed herein include, but are not limited to, non-pluripotent cells, incompletely or partially pluripotent stem cells, multipotent cells, oligopotent cells, unipotent cells, terminally differentiated cells, or a mixed population of cells comprising any combination of the foregoing. In some aspects, mononuclear cells that are cultured and expanded include, but are not limited to, hematopoetic stem and progenitor cells (e.g. CD34+ cells), myeloid progenitor cells, lymphoid progenitor cells, mast cells, monocytes, lymphocytes, cytotoxic T cells, helper T cells, regulatory T cells, natural killer T cells, memory T cells, B-cells (e.g. plasma B cells, memory B cells, B-1 cells and B-2 cells), neutrophils, macrophages, basophils, dendritic cells and eosinophils. Mononuclear cells expanded and cultured according to the invention may be used reprogrammed to iPSC, or used for banking (e.g. creating a repository of cells for potential therapeutic use).

A minimal volume of blood for use with the invention may comprise any volume that provides a number of mononuclear cells sufficient to achieve reprogramming as disclosed herein. Minimal volumes of blood for reprogramming may be between about 50 µl, and about 1 ml. Minimal volumes of blood may be about 900 µl, about 800 µl, about 700 µl, about 600 µl, about 500 µl, about 400 µl, about 300 µl, about 200 µl, about 100 µl about 50 µl, as well as any volume intervening these specifically specified volumes. In some embodiments, a minimal volume of blood is an amount of UCB blood provided in a cord blood segment. The minimal volume of blood may comprise a volume of blood sufficient to contain at least about 100 mononuclear cells. The minimal volume of blood may comprise a volume of blood sufficient to contain a number of mononuclear cells that is about 100, 1,000, $1 \times 10^3$, $1 \times 10^4$, $1 \times 10^5$ or $1 \times 10^6$ cells, as well as any number of cells intervening these amounts. The minimal volume of blood may contain less than about $1 \times 10^3$ mononuclear cells.

In some aspects of the invention, small molecules are used in the reprogramming of mononuclear cells. Accordingly, in particular embodiments, reprogramming mononuclear cells comprises introducing one or more reprogramming factors into the cells as contemplated herein and contacting the cells with at least one of a GSK3 inhibitor; a MEK inhibitor; a TGFβR inhibitor, and a Rho Kinase (ROCK) inhibitor. Such reprogramming procedures may improve the efficiency of reprogramming mononuclear cells. Improvements in efficiency of reprogramming can be measured by (1) a decrease in the time required for reprogramming and generation of pluripotent cells (e.g., by shortening the time to generate pluripotent cells by at least a day compared to a similar or same process without the small molecule), or alternatively, or in combination, (2) an increase in the number of pluripotent cells generated by a particular process (e.g., increasing the number of cells reprogrammed in a given time period by at least 10%, 30%, 50%, 100%, 200%, 500%, etc. compared to a similar or same process without the small molecule). In some embodiments, a 2-fold to 20-fold improvement in reprogramming efficiency is observed. In some embodiments, reprogramming efficiency is improved by more than 20 fold. In some embodiments, a more than 100 fold improvement in efficiency is observed over the method without the small molecule reprogramming agent (e.g., a more than 100 fold increase in the number of pluripotent cells generated).

In one embodiment, reprogramming mononuclear cells comprises introducing one or more reprogramming factors into the mononuclear cells as contemplated herein and contacting the cells with a GSK3 inhibitor; a MEK inhibitor; and a TGFβR inhibitor, and optionally a ROCK inhibitor. In another embodiment, reprogramming mononuclear cells comprises introducing one or more reprogramming factors into the cells as contemplated herein and contacting the cells with a GSK3 inhibitor; a MEK inhibitor; a TGFβR inhibitor, and a ROCK inhibitor.

In some aspects, reprogrammed mononuclear cells are cultured in the presence of one or more of a GSK-3 inhibitor, a MEK inhibitor, and optionally a ROCK inhibitor, wherein the cell culture medium does not comprise, or is essentially free of, an inhibitor of TGFβ/activin signaling pathways, including TGFβ receptor (TGFβR) inhibitors and ALK5 inhibitors, as contemplated herein. Without wishing to be bound to any particular theory, it is contemplated that long-term culture of pluripotent cells with a TGFβR/ALK5 inhibitor leads to spontaneous differentiation of the reprogrammed mononuclear cells. Thus, culturing reprogrammed mononuclear cells in the presence of a GSK-3 inhibitor, a MEK inhibitor, and a Rho Kinase (ROCK) inhibitor, but not a TGFβR/ALK5 inhibitor, may provide ground state pluripotent cells.

In particular embodiments, a mononuclear cell is reprogrammed by the methods disclosed herein and subsequently, the reprogrammed mononuclear cell is cultured to a stable ground state of pluripotency by culturing the cell in a medium comprising a GSK-3 inhibitor, a MEK inhibitor, and a Rho Kinase (ROCK) inhibitor, wherein the media lacks a TGFβR/ALK5 inhibitor.

In some embodiments, a mononuclear cell is reprogrammed by introducing one or more reprogramming factors and culturing the cell in a medium comprising a GSK-3 inhibitor, a MEK inhibitor, a Rho Kinase (ROCK) inhibitor, and a TGFβR/ALK5 inhibitor, and subsequently, the reprogrammed mononuclear cell is cultured to a provide cells with reduced spontaneous differentiation by culturing the cell in a medium comprising a GSK-3 inhibitor, a MEK inhibitor, and a Rho Kinase (ROCK) inhibitor, wherein the media lacks a TGFβR/ALK5 inhibitor.

One aspect concerns the GSK-3 inhibitors for use with the methods and compositions disclosed herein. GSK-3β inhibitors are specific exemplary Wnt pathway agonists suitable for use in compositions contemplated herein, and may include, but are not limited to, polynucleotides, polypeptides, and small molecules. GSK-3β inhibitors contemplated herein may decrease GSK-3β expression and/or GSK-3β activity. Illustrative examples of GSK-3β inhibitors contemplated herein include, but are not limited to, anti-GSK-3β antibodies, dominant negative GSK-3β variants, siRNA, shRNA, miRNA and antisense nucleic acids that target GSK-3β.

Other illustrative GSK-3β inhibitors include, but are not limited to: Kenpaullone, 1-Azakenpaullone, CHIR99021, CHIR98014, AR-A014418, CT 99021, CT 20026, SB216763, AR-A014418, lithium, SB 415286, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione; TWS1 19 pyrrolopyrimidine compound, L803 H-KEAPPAPPQSpP-NH2 or its myristoylated form; 2-Chloro-1-(4,5-dibromo-thiophen-2-yl)-ethanone; GF109203X; RO318220; TDZD-8; TIBPO; and OTDZT.

In particular illustrative embodiments, the GSK-3β inhibitor is CHIR99021, BIO, or Kenpaullone. In a preferred embodiment, the GSK-3β inhibitor is CHIR99021.

An aspect of the invention concerns the MEK inhibitors for use with the methods and compositions disclosed herein. ERK/MEK inhibitors suitable for use in methods and compositions contemplated herein include, but are not limited to, polynucleotides, polypeptides, and small molecules. ERK/MEK inhibitors contemplated herein may decrease MEK or ERK expression and/or MEK or ERK activity. Illustrative examples of MEK/ERK inhibitors contemplated herein include, but are not limited to, anti-MEK or anti-ERK antibodies, dominant negative MEK or ERK variants, siRNA, shRNA, miRNA and antisense nucleic acids that target MEK or ERK.

Other illustrative ERK/MEK inhibitors include, but are not limited to, PD0325901, PD98059, UO126, SL327, ARRY-162, PD184161, PD184352, sunitinib, sorafenib, Vandetanib, pazopanib, Axitinib, GSK1 120212, ARRY-438162, RO5126766, XL518, AZD8330, RDEA1 19, AZD6244, FR180204 and PTK787.

Additional illustrative MEK/ERK inhibitors include those compounds disclosed in International Published Patent Applications WO 99/01426, WO 02/06213, WO 03/077914, WO 05/051301 and WO2007/044084.

Further illustrative examples of MEK/ERK inhibitors include the following compounds: 6-(4-Bromo-2-chloro-phenylamino)-7-fluoro-3-methyl-3H-benzoimidazol-e-5-carboxylic acid (2,3-dihydroxy-propoxy)-amide; 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimida-zol-5-yl]-2-hydroxy-ethanone, 6-(4-Bromo-2-chloro-phenylamino)-7-fluoro-3-methyl-3H-benzoimidazol-e-5-carboxylic acid (2-hydroxy-1,1-dimethyl-ethoxy)-amide, 6-(4-Bromo-2-chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazol-e-5-carboxylic acid (2-hydroxy-ethoxy)-amide, referred to hereinafter as MEK inhibitor 1; 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6-oxo-1,6-dihydro-pyridazine-3-carboxamide or a pharmaceutically acceptable salt thereof.

In a preferred embodiment, the MEK/ERK inhibitor is PD98059.

One aspect of the invention concerns the ROCK inhibitors for use with the methods and compositions disclosed herein. Rho associated kinases (ROCK) are serine/threonine kinases that serve downstream effectors of Rho kinases (of which three isoforms exist-RhoA, RhoB and RhoC). ROCK inhibitors suitable for use in the methods and compositions contemplated herein include, but are not limited to, polynucleotides, polypeptides, and small molecules. ROCK inhibitors contemplated herein may decrease ROCK expression and/or ROCK activity. Illustrative examples of ROCK inhibitors contemplated herein include, but are not limited to, anti-ROCK antibodies, dominant negative ROCK variants, siRNA, shRNA, miRNA and antisense nucleic acids that target ROCK.

Illustrative ROCK inhibitors contemplated herein include, but are not limited to: thiazovivin, Y27632, Fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, and (R)-(+)-trans-N-(4-Pyridyl)-4-(1-aminoethyl)-cyclohexanecarboxamide and ROCK inhibitors disclosed in U.S. Pat. No. 8,044,201, which is herein incorporated by reference in its entirety.

In one embodiment, the ROCK inhibitor is thiazovivin, Y27632, or pyrintegrin.

In a preferred embodiment, the ROCK inhibitor is thiazovivin.

An aspect of the invention concerns the TGFβ receptor (e.g., ALK5) inhibitors for use with the methods and compositions disclosed herein. Suitable TGFβ receptor (e.g., ALK5) inhibitors for use with the invention can include antibodies to, dominant negative variants of, and antisense nucleic acids that suppress expression of, TGFβ receptors (e.g., ALK5). Exemplary TGFβ receptor/ALK5 inhibitors include, but are not limited to, SB431542 (see, e.g., Inman, et al., Molecular Pharmacology 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., Cancer Science 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (−{4-[3-(pyridin-2-yl)-1H-pyrazol-4-yl]pyridin-2-yl}-N-(tetrahydro-2H-pyran-4-yl)benzamide) (see, e.g., Gellibert, et al., Journal of Medicinal Chemistry 49(7):2210-2221 (2006)), SM16 (see, e.g., Suzuki, et al., Cancer Research 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., Xenobiotica 38(3):325-339 (2008)), GW6604 (2-phenyl-4-(3-pyridin-2-yl-1H-pyrazol-4-yl)pyridine) (see, e.g., de Gouville, et al., Drug News Perspective 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., Molecular Pharmacology 65(3):744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data herein showing the effect of inhibiting ALK5, it is believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described herein. Exemplary TGFβ/activin pathway inhibitors include but are not limited to: TGFβ receptor inhibitors, inhibitors of SMAD ⅔ phosphorylation, inhibitors of the interaction of SMAD ⅔ and SMAD 4, and activators/agonists of SMAD 6 and SMAD 7.

TGFβ receptor inhibitors can include antibodies to, dominant negative variants of and siRNA or antisense nucleic acids that target TGFβ receptors. Specific examples of TGFβ receptor inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., Clinical Cancer Research 13(18):5262-5270 (2007); Kaminska, et al., Acta Biochimica Polonica 52(2):329-337 (2005); and Chang, et al., Frontiers in Bioscience 12:4393-4401 (2007).)

Inhibitors of SMAD ⅔ phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et al., EP1992360, incorporated herein by reference.)

Inhibitors of the interaction of SMAD ⅔ and smad4 can include antibodies to, dominant negative variants of and antisense nucleic acids that target SMAD2, SMAD3 and/or smad4. Specific examples of inhibitors of the interaction of SMAD ⅔ and SMAD4 include but are not limited to Trx-SARA, Trx-xFoxH1b and Trx-Lefl. (See, e.g., Cui, et al., Oncogene 24:3864-3874 (2005) and Zhao, et al., Molecular Biology of the Cell, 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO-oligonucleotides. (See, e.g., Miyazono, et al., U.S. Pat. No. 6,534,476, and Steinbrecher, et al., US2005119203, both incorporated herein by reference.

In some aspects, the invention provides compositions comprising a minimal volume of blood comprising mononuclear cells and at least one of the reprogramming factors disclosed herein. The composition may comprise a minimal volume of UCB comprising mononuclear cells and at least one reprogramming factor disclosed herein. The composition may comprise a cord blood segment comprising mononuclear cells and at least one reprogramming factor disclosed herein. The composition may comprise a minimal volume of blood comprising mononuclear cells and at least one of OCT4, SOX2, KLF4 and c-MYC. The composition may comprise a minimal volume of blood comprising mononuclear cells and at least one of OCT4, SOX2, KLF4 and LIN28. The composition may comprise a minimal volume of UCB comprising mononuclear cells and at least one of OCT4, SOX2, KLF4 and c-MYC. The composition may comprise a minimal volume of blood comprising mononuclear cells and at least one of OCT4, SOX2, KLF4 and LIN28. The composition may comprise a minimal volume of blood comprising mononuclear cells and at least one of OCT4, NANOG, ECAT1, ESRRB, and UTF1. The composition may comprise a minimal volume of UCB comprising mononuclear cells and at least one of OCT4, NANOG, ECAT1, ESRRB, and UTF1. The composition may comprise a minimal volume of blood comprising mononuclear cells and at least one of OCT4, SOX2, and SV40LT. The composition may comprise a minimal volume of UCB comprising mononuclear cells and at least one of OCT4, SOX2, and SV40LT. The composition may comprise a minimal volume of blood comprising mononuclear cells and at least one of OCT4, ECAT1, and UTF1. The composition may comprise a minimal volume of UCB comprising mononuclear cells and at least one of OCT4, ECAT1, and UTF1.

In some aspects, the invention provides compositions comprising a minimal volume of blood comprising mononuclear cells, at least one of the reprogramming factors disclosed herein, and at least one of a GSK3 inhibitor; a MEK inhibitor; a TGFβR inhibitor, and a ROCK inhibitor. The composition may comprise a minimal volume of UCB comprising mononuclear cells, at least one reprogramming factor disclosed herein, and at least one of a GSK3 inhibitor; a MEK inhibitor; a TGFβR inhibitor, and a ROCK inhibitor. The composition may comprise a cord blood segment comprising mononuclear cells, at least one reprogramming factor disclosed herein, and at least one of a GSK3 inhibitor; a MEK inhibitor; a TGFβR inhibitor, and a ROCK inhibitor. The composition may comprise a minimal volume of blood comprising mononuclear cells, at least one of OCT4, SOX2, KLF4 and c-MYC, and at least one of a GSK3 inhibitor; a MEK inhibitor; a TGFβR inhibitor, and a ROCK inhibitor. The composition may comprise a minimal volume of blood comprising mononuclear cells, at least one of OCT4, SOX2, KLF4 and LIN28, and and at least one of a GSK3 inhibitor; a MEK inhibitor; a TGFβR inhibitor, and a Rho Kinase (ROCK) inhibitor. The composition may comprise a minimal volume of UCB comprising mononuclear cells, at least one of OCT4, SOX2, KLF4 and c-MYC, and at least one of a GSK3 inhibitor; a MEK inhibitor; a TGFβR inhibitor, and a ROCK inhibitor. The composition may comprise a minimal volume of blood comprising mononuclear cells, at least one of OCT4, SOX2, KLF4 and LIN28, and at least one of a GSK3 inhibitor; a MEK inhibitor; a TGFβR inhibitor, and a ROCK inhibitor. The composition may comprise a minimal volume of blood comprising mononuclear cells, at least one of OCT4, NANOG, ECAT1, ESRRB, and UTF1, and at least one of a GSK3 inhibitor; a MEK inhibitor; a TGFβR inhibitor, and a ROCK inhibitor. The composition may comprise a minimal volume of UCB comprising mononuclear cells, at least one of OCT4, NANOG, ECAT1, ESRRB, and UTF1, and at least one of a GSK3 inhibitor; a MEK inhibitor; a TGFβR inhibitor, and a ROCK inhibitor. The composition may comprise a minimal volume of blood comprising mononuclear cells, at least one of OCT4, SOX2, and SV40LT, and at least one of a GSK3 inhibitor; a MEK inhibitor; a TGFβR inhibitor, and a ROCK inhibitor. The composition may comprise a minimal volume of UCB comprising mononuclear cells, at least one of OCT4, SOX2, and SV40LT, and at least one of a GSK3 inhibitor; a MEK inhibitor; a TGFβR inhibitor, and a ROCK inhibitor. The composition may comprise a minimal volume of blood comprising mononuclear cells, at least one of OCT4, ECAT1, and UTF1, and at least one of a GSK3 inhibitor; a MEK inhibitor; a TGFβR inhibitor, and a ROCK inhibitor. The composition may comprise a minimal volume of UCB comprising mononuclear cells, at least one of OCT4, ECAT1, and UTF1, and at least one of a GSK3 inhibitor; a MEK inhibitor; a TGFβR inhibitor, and a ROCK inhibitor.

In some aspects, the invention provides compositions comprising between about 100 to about $1 \times 10^4$ mononuclear cells and at least one of the reprogramming factors disclosed herein. The composition may comprise between about 100 to about $1 \times 10^4$ mononuclear cells and at least one of OCT4, SOX2, KLF4 and c-MYC. The composition may comprise between about 100 to about $1 \times 10^4$ mononuclear cells and at least one of OCT4, SOX2, KLF4 and LIN28. The composition may comprise between about 100 to about $1 \times 10^4$ mononuclear cells and at least one of OCT4, SOX2, KLF4 and c-MYC. The composition may comprise between about 100 to about $1 \times 10^4$ mononuclear cells and at least one of OCT4, SOX2, KLF4 and LIN28. The composition may comprise between about 100 to about $1 \times 10^4$ mononuclear cells and at least one of OCT4, NANOG, ECAT1, ESRRB, and UTF1. The composition may comprise between about 100 to about $1 \times 10^4$ mononuclear cells and at least one of OCT4, NANOG, ECAT1, ESRRB, and UTF1. The composition may comprise about 100 to about $1 \times 10^4$ mononuclear cells and at least one of OCT4, SOX2, and SV40LT. The composition may comprise about 100 to about $1 \times 10^4$ mononuclear cells and at least one of OCT4, SOX2, and SV40LT. The composition may comprise about 100 to about 1×10⁴ mononuclear cells and at least one of OCT4, ECAT1, and UTF1. The composition may comprise about 100 to about 1×10⁴ mononuclear cells and at least one of OCT4, ECAT1, and UTF1.

In some aspects, the invention provides compositions comprising about 100 to about 1×10⁴ mononuclear cells, at least one of the reprogramming factors disclosed herein, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, KLF4 and c-MYC, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, KLF4 and LIN28, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, KLF4 and c-MYC, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, KLF4 and LIN28, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, NANOG, ECAT1, ESRRB, and UTF1, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, NANOG, ECAT1, ESRRB, and UTF1, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, and SV40LT, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, SOX2, and SV40LT, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, ECAT1, and UTF1, and at least one of a GSK3 inhibitor; a MEK inhibitor; a TGFβR inhibitor, and a ROCK inhibitor. The composition may comprise about 100 to about 1×10⁴ mononuclear cells, at least one of OCT4, ECAT1, and UTF1, and at least one of a GSK3 inhibitor; a MEK inhibitor; a TGFβR inhibitor, and a ROCK inhibitor.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

Example 1

CD34+ Cell Selection and Cell Expansion (Including Expansion Media)

Blood cells derived from fresh or frozen peripheral or umbilical cord blood collected in minimal volumes, such as 500 or 100 μL from cord blood segments, were processed by either; 1) Ficoll enrichment for mononuclear cells followed by hematopoietic stem cell culture and expansion and subsequent flow cytometry sort for CD45+/CD34+/Lineage− cells prior to reprogramming (FIG. 2A), or 2) initially flow cytometry sorted for CD34+/CD45+/Lineage-population expanded in hematopoietic stem cell culture medium (FIG. 2C) followed by reprogramming. Cells expanded efficiently under the culture conditions (FIG. 2B) and produced a homogenous population of cells as demonstrated by cell flow profile for Lin and CD34 (FIG. 2D). Hematopoietic stem cell media consisted of serum free base medium SFM (Stem Cell Technologies) supplemented with cytokines stem cell factor (SCF) ranging 10-100 ng/mL, Thrombopoietin (TPO) ranging 10-100 ng/mL, FLT3L ranging 10-100 ng/mL, basic fibroblast growth factor (bFGF) ranging 5-50 ng/mL and insuling growth factor (IGF) ranging 5-50 ng/mL. SFM was optionally replaced with Iscoves MEM (Corning) supplemented with serum replacement cocktail or insulin/transferrin/selenium (Sigma). Collected blood cells were resuspended in hematopoietic stem cell medium and transferred to previously matrigel (Corning) coated wells. Every 2 to 3 days the culture received additional fresh medium and pipette up and down to break up cell clumps formed during suspended culture proliferation. Cells were readily transfected as demonstrated by GFP expression (FIG. 2E).

Example 2

Reprogramming Mononuclear Cells

To initiate reprogramming, ectopic expression of reprogramming factors was induced by lentiviral transduction or episomal vector transfection. Lentiviral transfection was followed as previously described (Valamehr et al. Sci Rep. 2012; 2:213). Briefly, the cells from Example 1 were plated at 1×10⁵ cells per well of a 6-well plate on Matrigel (BD Biosciences) coated surface. Unless specified, all Matrigel coatings consists of adding Matrigel solution (one aliquot of Matrigel resuspended in 25 mL DMEM/F12) to tissue culture surfaces and allowing for 2-4 hrs incubation at 37° C. Supernatant from 293T cells generating lentivirus expressing transgene OCT4/SOX2/SV40LT was added to the starting cells at a dilution of 1:2 (one part lentiviral supernatant: one part fibroblast medium), supplemented with 4 μg/mL polybrene (Millipore), and transferred to 37° C. and 5% CO₂ for 12-16 hrs. For episomal vector reprogramming, transfection of cord blood cells using gene set OCT4/SOX2/SV40LT (A14703, Life Technologies) was conducted using NEON Transfection System (Life Technologies). Approximately, 4 μg of vector set was transfected into 2.5×10⁵ cord blood cells using settings 1650 v/10 ms/3 pulses in appropriate buffers as described by product manual. The transfected cells were plated directly into a 10 cm dish (fibroblast) or a well of 6-well plate (cord blood) coated with Matrigel and containing hematopoietic stem cell medium (see above) supplemented with 10 ng/mL bFGF and 5 µg/mL fibronectin (BD Biosciences). Twenty-four hours post transfection, FRM was added to the culture in equal volume. The culture medium was switched to entirely FRM on day 5 with hygromycin removed on day 7 post transfection. All reprogramming cultures were switched to FMM on day 14 post transfection. Cell flow cytometry profile demonstrated expression of SSEA4 and TRA181 and an iPSC phenotype (FIGS. 3A and 3B). Twenty-four hours post transfection, FRM was added in equal volume and continuously added every few days until day 14 post transfection where the culture was aspirated and replaced with entirely FMM. Clusters of adherent rounded cells were seen around days 5 to 7 post transfection. Once in FMM, reprogramming cultures were maintained and single cell passaged using Accutase on either Matrigel or Vitronectin coated surface. The single cell dissociated cells were expanded onto Matrigel coated plates with FMM and maintained until flow cytometry sorting. Reprogramming efficiency was determined by cell flow analysis of SSEA4 and TRA181 and colony counts (FIG. 3A), as well the expression of NANOG (FIG. 3B). In Vitronectin (Life Technologies) surface coating studies, all aspects were kept the same except for the substitution of Matrigel for Vitronectin. For reduced factor episomal reprogramming, pCEP4 (Life Technologies) vector backbone was constructed to contain OCT4-P2A-OCT4, OCT4-P2A-SOX2 or OCT4-P2A-NANOG-T2A-SOX2 under the regulation of EF1α promoter. The transfection of reduced factor episomal vectors followed the same protocol as described above with the exception of few modifications. EBNA was co-transfected as either EBNA mRNA (20 µg) or vector cassette (2 µg) (Howden et al., 2006). Hygromycin selection was maintained for 10 days and FMM was introduced on day 16.

Example 3

H₁PSC Maintenance in Small Molecule Culture

Figure 4A:
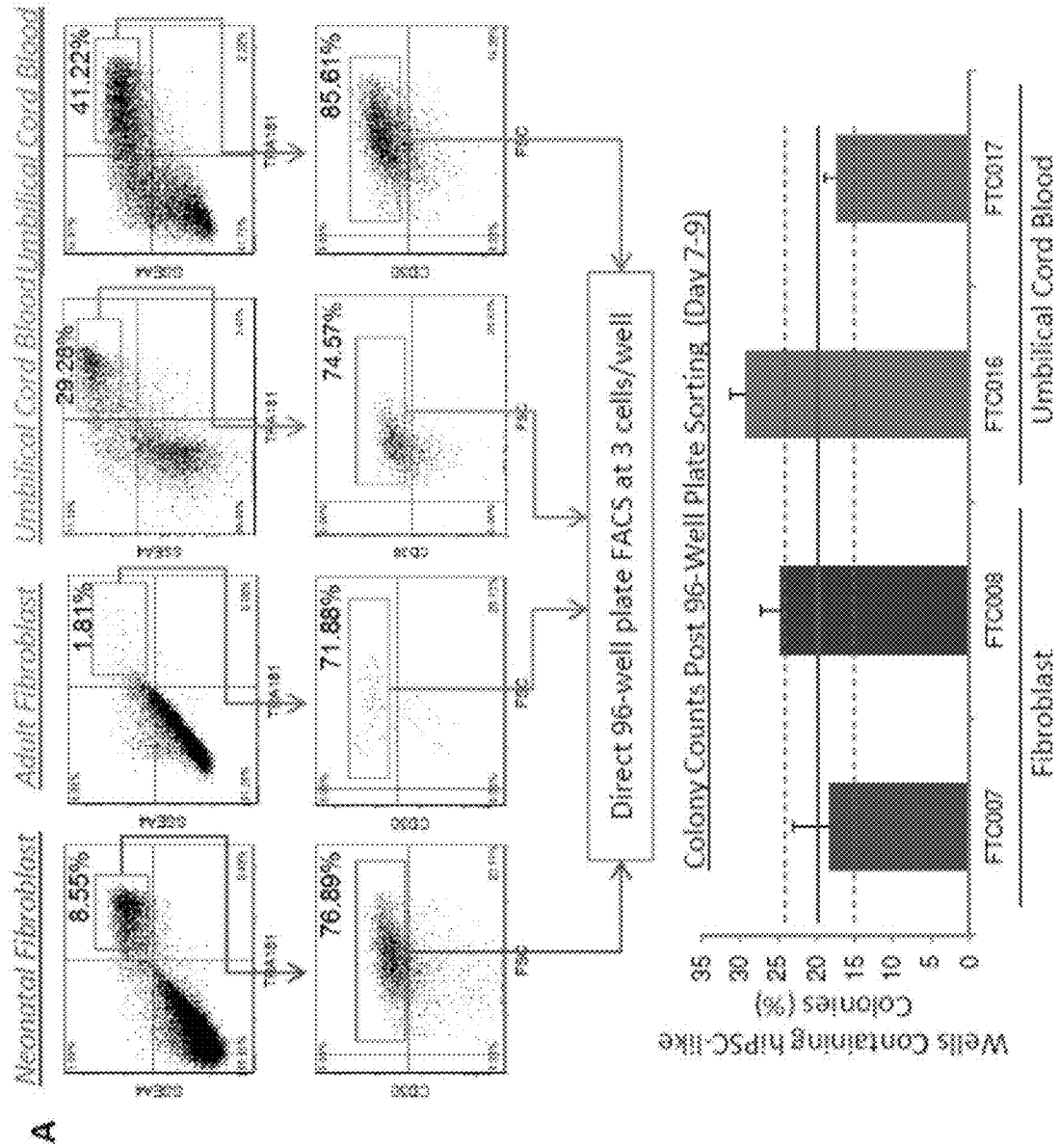
FIGS. 4A-4E. Episomal reprogrammed hiPSCs are readily sorted as individual cells, maintain their undifferentiated state, and are free of transgenes.
Figure 4B:
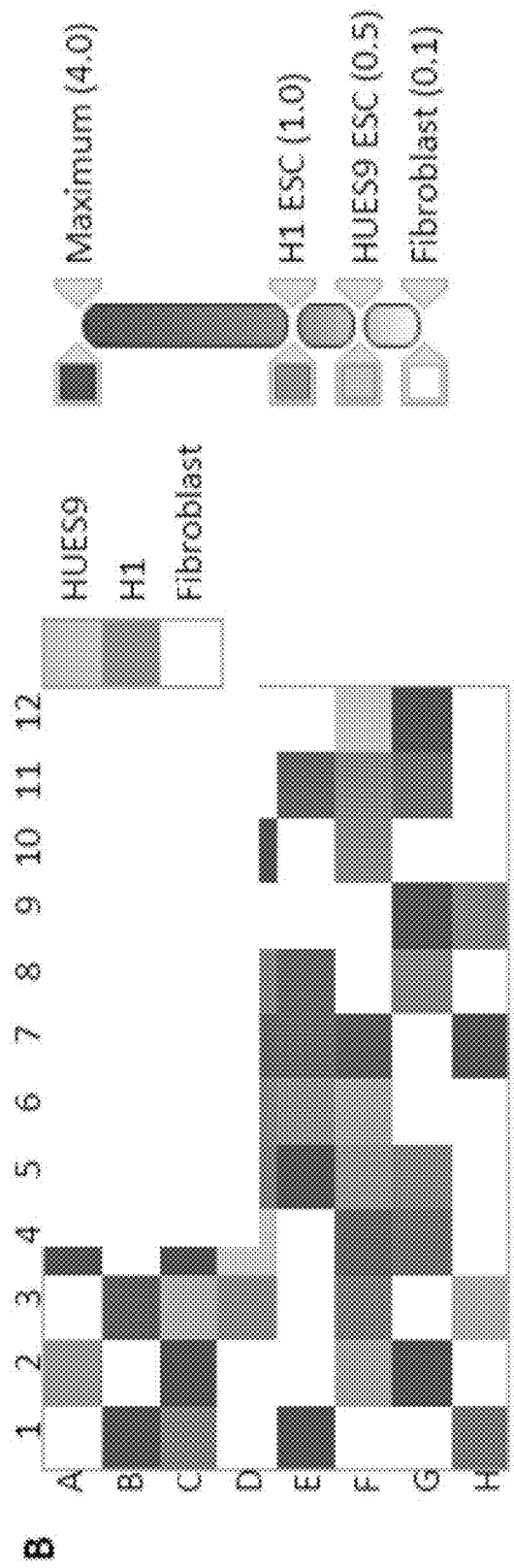
Figure 4C:
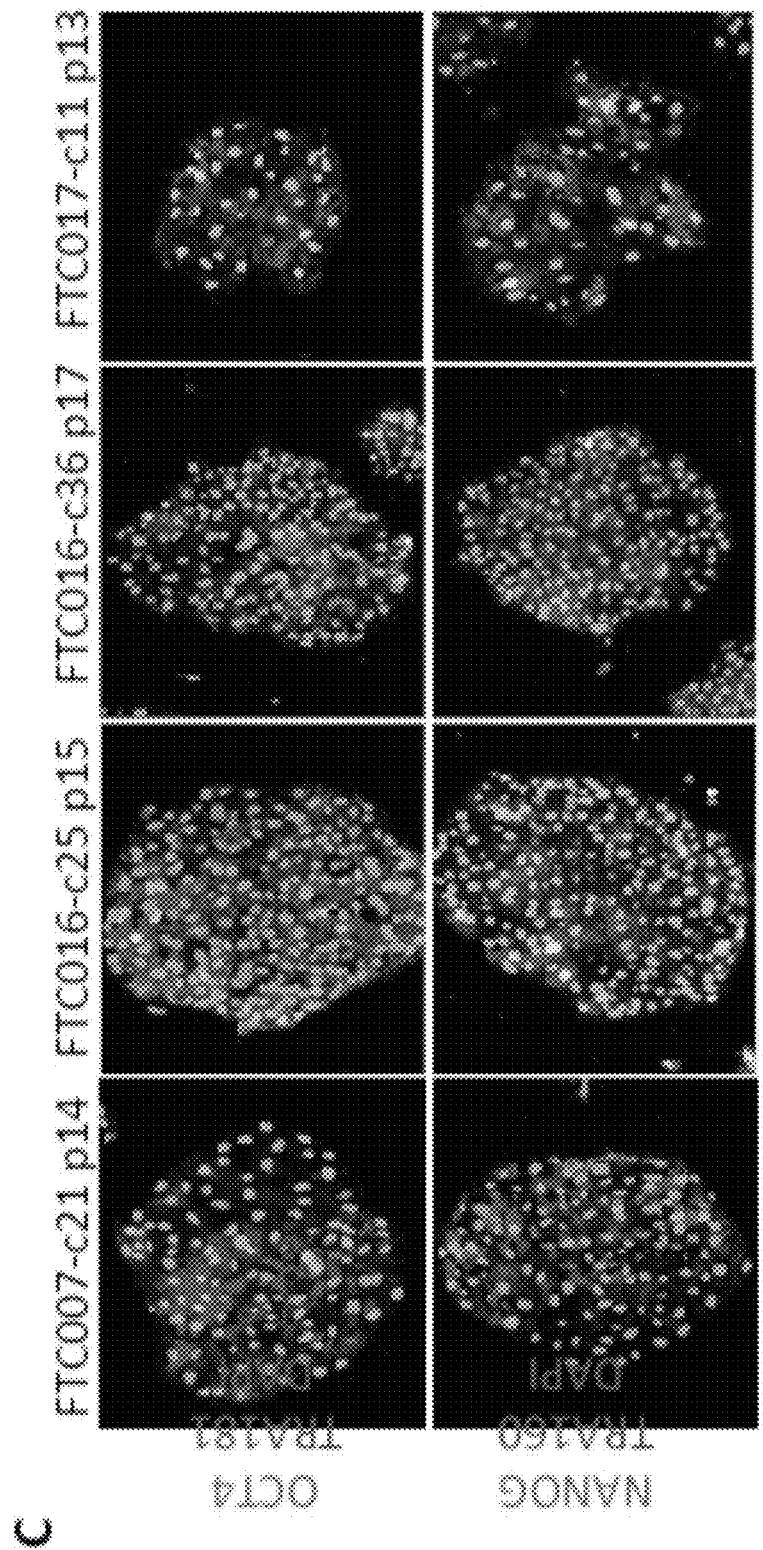
Figure 4D:
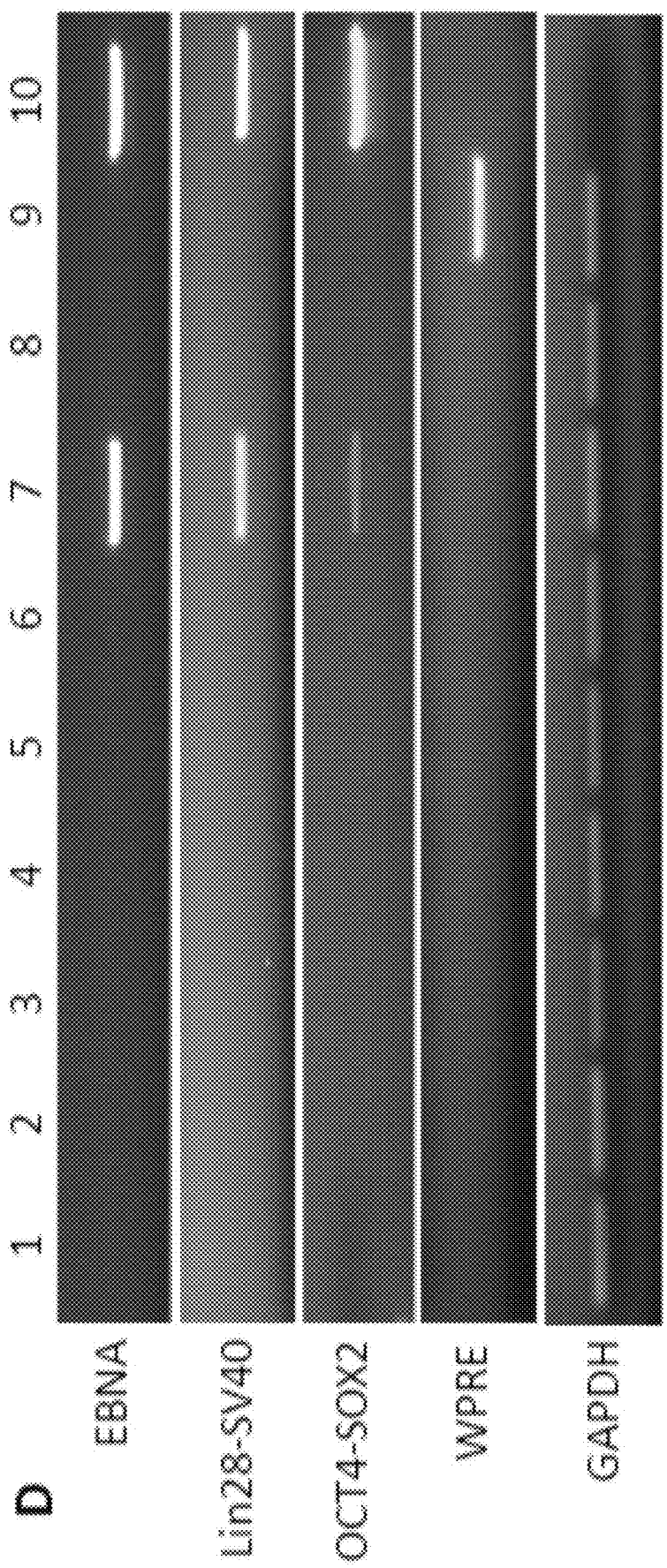
Figure 4E:
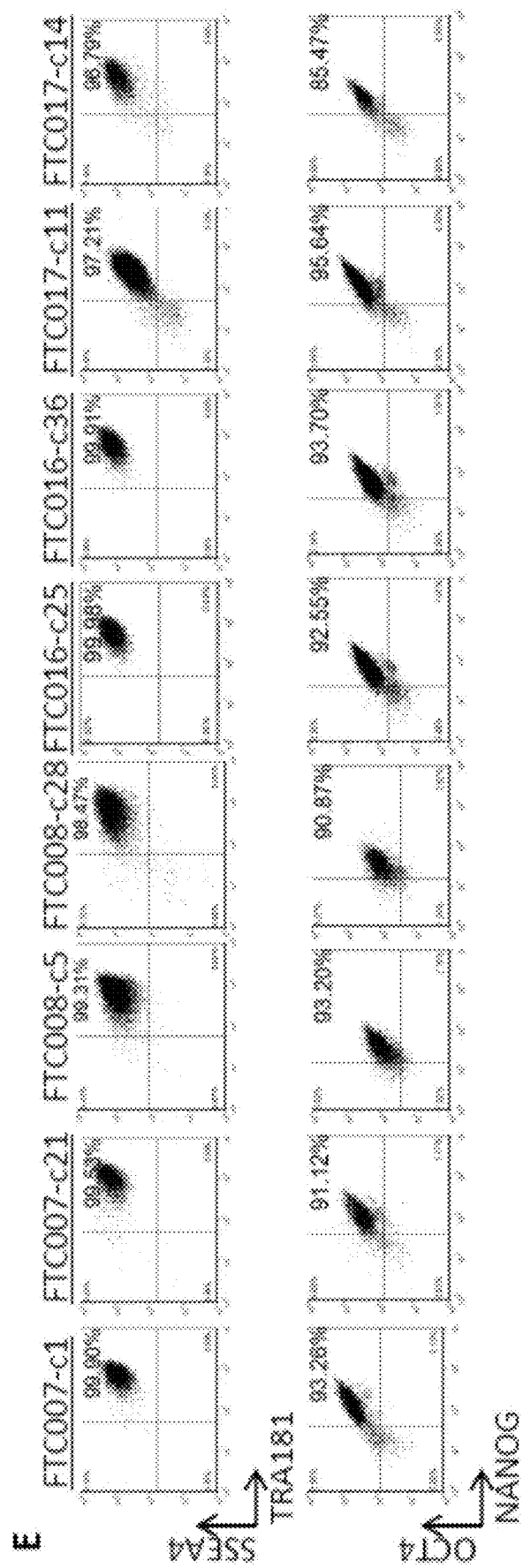
Figure 5A:
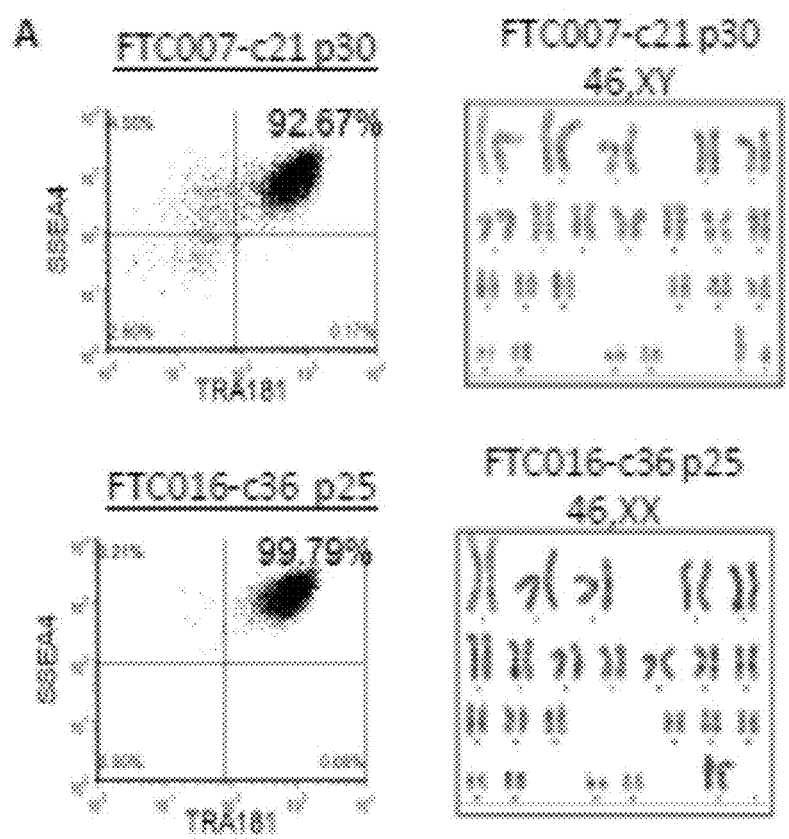
FIGS. 5A-5D. Genomic stability and pluripotency are maintained during continuous single cell and feeder-free culture.

Derived hiPSCs according to Example 2 were routinely passaged in feeder free culture as single cells once confluency of the culture reached 75-90%. Cells were maintained in FMM. Cultured cells showed expression of pluripotency markers OCT4, NANOG, TRA181, TRA160, and DAPI (FIG. 4C) and formed a homogenous population of undifferentiated cells as demonstrated by cell flow detection of NANOG, SSEA4 and TRA181 (FIGS. 4E and 5A). Overconfluency was seen to exhaust the medium and result in differentiation. For single cell dissociation, hiPSCs were washed once with phosphate buffered saline (PBS) (Mediatech) and treated with Accutase (Millipore) for 3 to 5 min at 37° C. followed with pipetting to ensure single cell dissociation. The single cell suspension was then mixed in equal volume with base medium that does not include small molecules serving as a wash medium, centrifuged at 225 g for 4 min, resuspened in FMM and plated on Matrigel coated surface. Passages were typically 1:6-1:8, transferred tissue culture plates previously coated with Matrigel for 2-4 hrs in 37° C. or Vitronectin for 1 hr at 25° C. and fed every two to three days with FMM. Cell cultures were maintained in a humidified incubator set at 37° C. and 5% $CO_2$. FMM culture is discussed previously (Valamehr et al. Sci Rep. 2012; 2:213)).

TABLE 1

| Conventional hESC Medium (Conv.) | Fate Reprogramming Medium (FRM) | Fate Maintenance Medium (FMM) |
|---|---|---|
| DMEM/F12 Knockout Serum Replacement (20%) | DMEM/F12 Knockout Serum Replacement (20%) N2 (1x) B27 (1x) | DMEM/F12 Knockout Serum Replacement (20%) |
| Glutamine (1x) Non-Essential Amino Acids β-mercaptoethanol bFGF (10 ng/mL) | Glutamine (1x) Non-Essential Amino Acids β-mercaptoethanol bFGF (100 ng/mL) LIF (10 ng/mL) Thiazovivin (5.0 µM) PD0325901 (0.4 µM) CHIR99021 (1.0 µM) SB431542 (2.0 µM) | Glutamine (1x) Non-Essential Amino Acids β-mercaptoethanol bFGF (100 ng/mL) LIF (10 ng/mL) Thiazovivin (5.0 µM) PD0325901 (0.4 µM) CHIR99021 (1.0 µM) |
| In combination with MEF | Feeder free, in combination with Matrigel or Vitronectin | |

Example 4

Reprogramming of a Minimal Volume of Mononuclear Cells

Figure 7A:
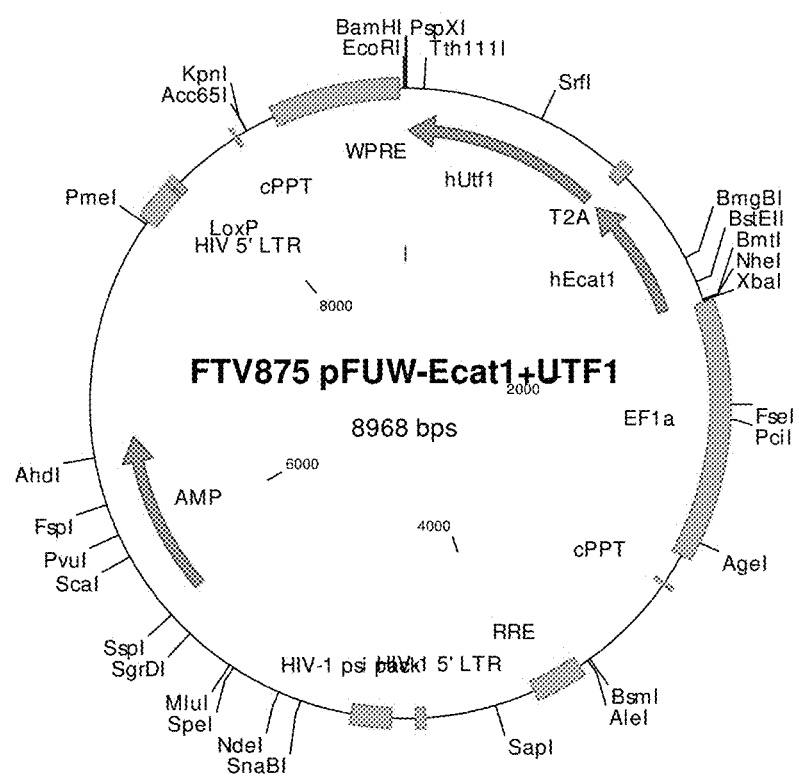
FIGS. 7A-7F show cloning maps illustrating examples of the lentiviral constructs (FIGS. 7A-7B) and episomal constructs (FIGS. 7C-7F) used for reprogramming. Lentiviral constructs include an EF1α promoter and a LOXP site for CRE-mediated excision of transgenes. Episomal constructs also include an EF1α promoter.
Figure 7B:
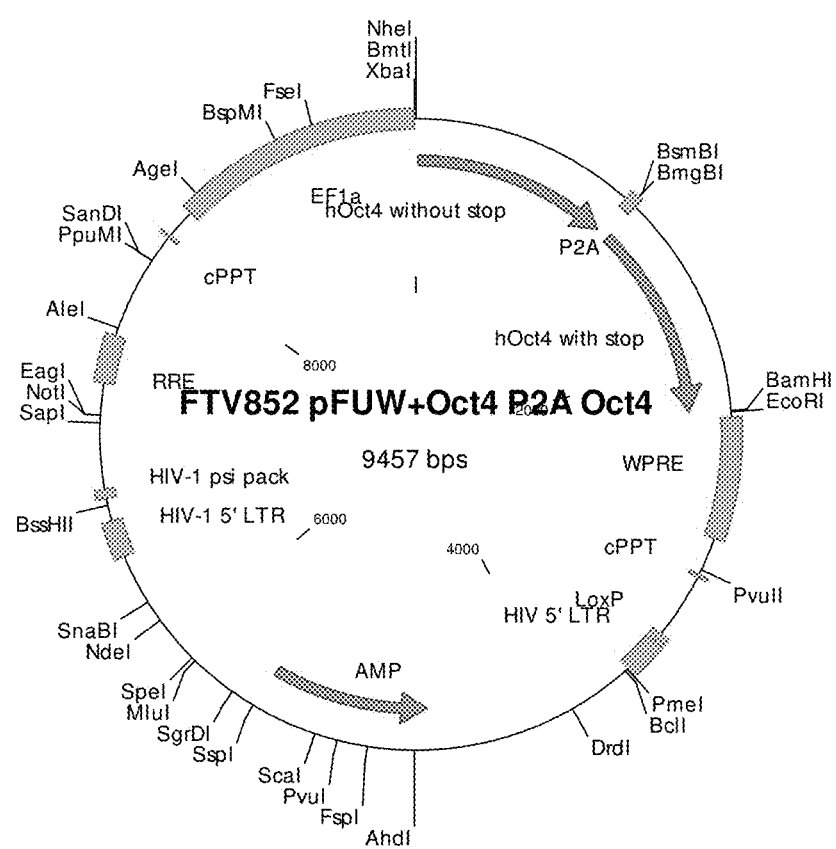
Figure 7C:
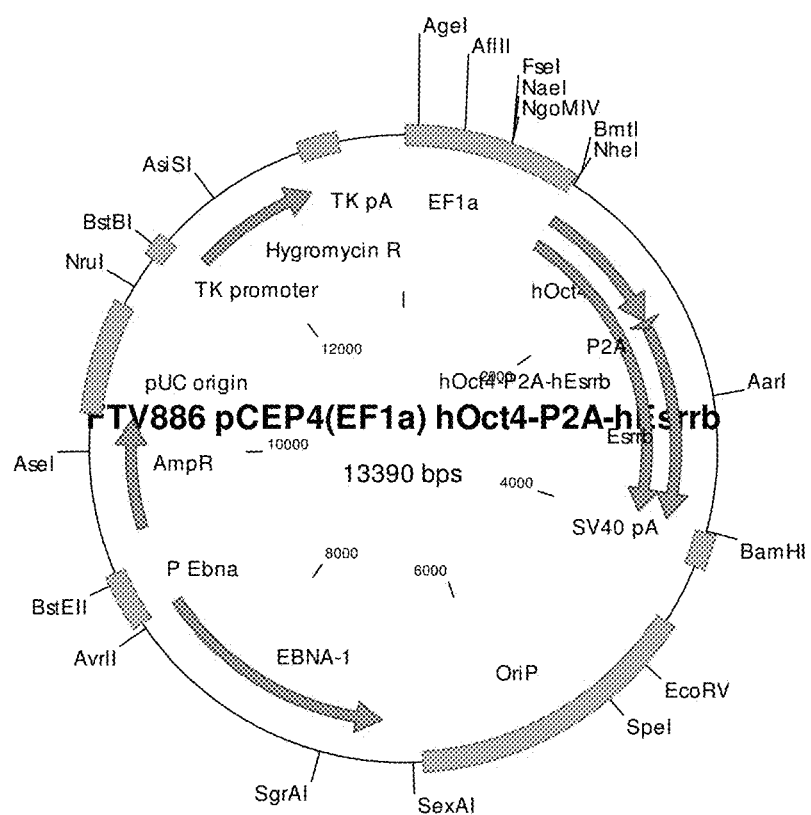
Figure 7D:
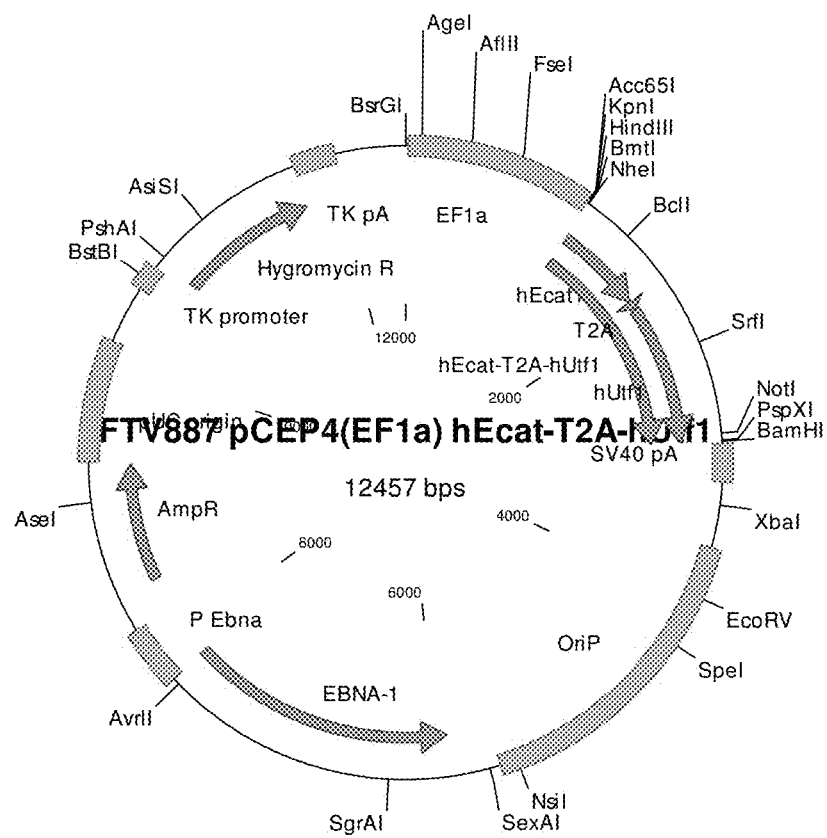
Figure 7E:
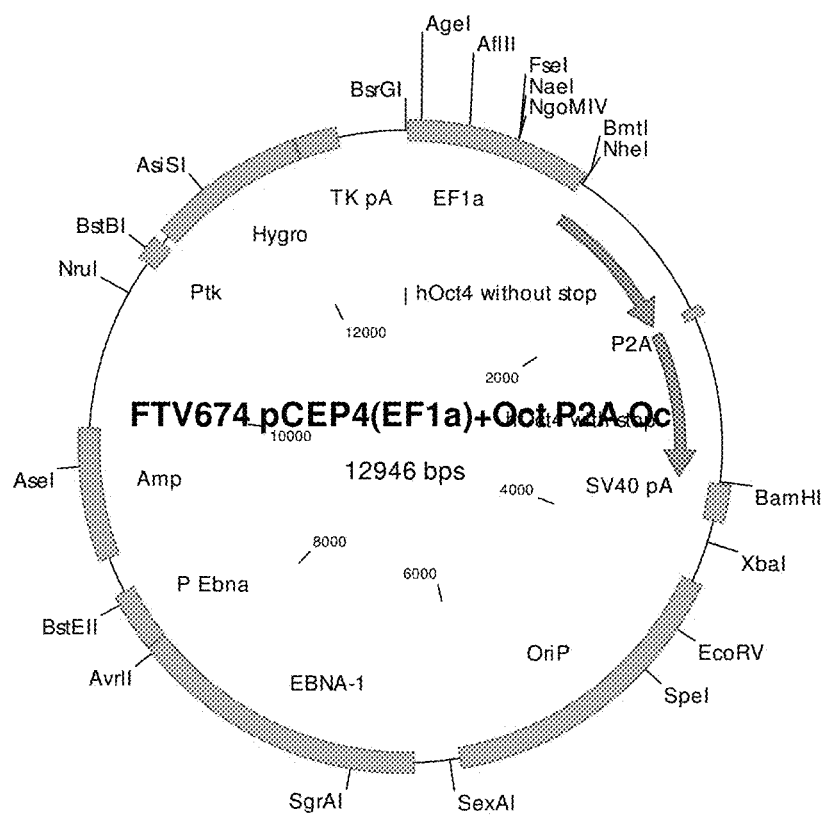
Figure 7F:
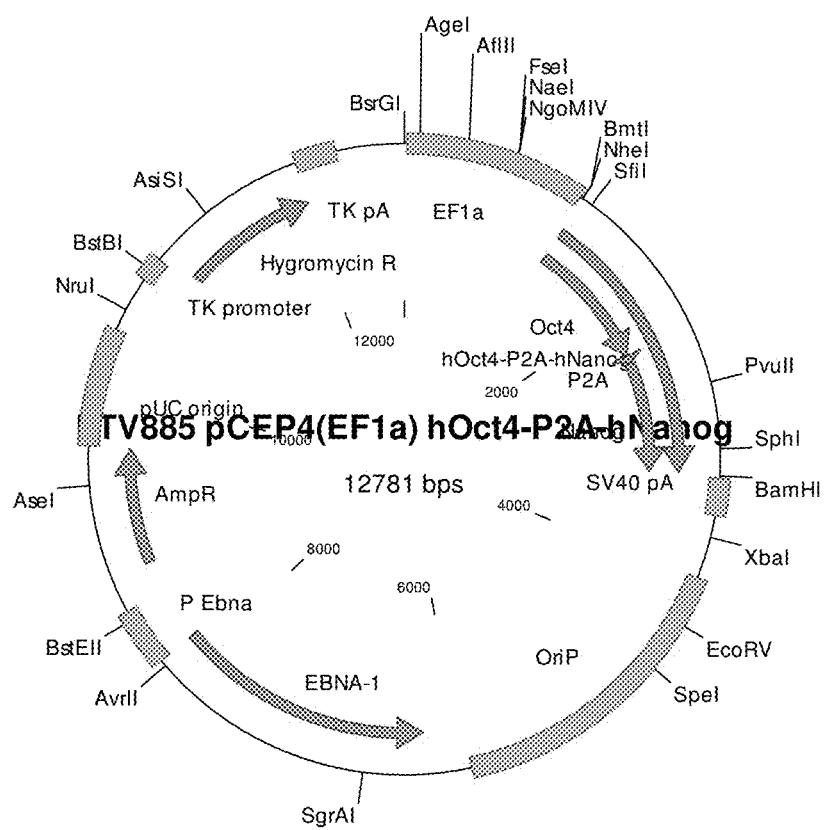

To initiate reprogramming, ectopic expression of reprogramming factors is induced by lentiviral transduction using NIL, traditional integrating lentivirus, or electroporation with episomal vectors. As illustrated in FIGS. 7A-B, the lentiviral expression system consists of several features including an EF1α promoter, specific gene combinations (Table 2) and a LOXP site at the 3' end to allow for CRE-mediated excision of the integrated transgenes. Upon CRE-excision, the derived hiPSCs genome no longer contains transgenes and are essentially footprint-free. As illustrated in FIGS. 7C-F, the episomal constructs have unique features including an EF1α promoter and unique reprogramming factors. Upon transfection, the episomal constructs reside in the nucleus and act in a trans-mediated fashion without integrating into the genome.

For lentivirus infection, the starting mononuclear cells or CD45+/CD34+/Lineage-cells are seeded at 100 to $1 \times 10^4$ cells per well of a 6-well plate coated with Matrigel (Corning) per manufacturer's instructions. Fresh lentiviral supernatant from 293T cells is added to the starting cells at a dilution of 1:2 (one part lentiviral supernatant: one part fibroblast medium). NIL viral supernatant is used at a 1× concentration and not diluted. If previously frozen virus is used, it is not diluted and used at a 1× concentration. Viral supernatants of various factors are combined (Table 2) up to a total of 2 mL of media per 6-well. This is supplemented with 5 µg/mL polybrene (Millipore) and 10 mM Hepes (Meditech) followed by spin infection. Six well plates are sealed with parafilm and centrifuged at 600 g for 90 min at 32° C. Plates are then transferred to 37° C. and 5% $CO_2$ incubators for 12-16 hrs. After incubation with lentivirus, the cells are washed with PBS and the culture medium switched to 50/50 medium containing one part FRM and one part hematopoietic medium (ISCOVES media+TPO, SCF, FLT3L). The medium is completely switched to FRM between 4 to 6 days post infection. FRM consists of conventional medium (described above) supplemented with 5 µM Thiazovivin (synthesized in-house), 0.4 µM PD0325901 (Biovision), 1 µM CHIR99021 (Biovision), 2 µM SB431542 (Biovision), 100 ng/mL bFGF (Life Technologies), 10 ng/mL hLIF (Millipore), 1× N2 Supplement (Life Technologies), and 1× B27 Supplement (Life Technologies). Once wells become confluent, cells are passaged onto 10 cm dishes previously coated with Matrigel. Passaging consists of dissociation with Accutase (Millipore) onto Matrigel coated surface (as described above). Between days 14 and 18 or when iPSC colonies become present, the culture media is switched from FRM to FMM. The single cell dissociated cells are expanded onto Matrigel coated plates with FMM and maintained until flow cytometry sorting.

TABLE 2

Reprogramming Factor Combinations Vector System

OCT4-P2A-OCT4
ECAT1-P2A-UTF1
OCT4-P2A-OCT4
NANOG-P2A-ESRRB-T2A-LIN28
ECAT1-P2A-UTF1
OCT4-P2A-ESRRB
OCT4-P2A-NANOG
ECAT1-P2A-UTF1
OCT4-P2A-NANOG
ECAT1-P2A-UTF1

For episomal vector reprogramming, transfection of mononuclear cells or CD45+/CD34+/Lineage− using the plasmids is conducted using the NEON Transfection System (Life Technologies). Approximately, a total of 3 µg of episomal plasmids containing reprogramming factors is co-transfected with EBNA (either in the form of mRNA or as a cassette in cloning plasmid pCDNA) into 100 to $1\times10^4$ cells using settings 1650 v/10 ms/3 pulses in appropriate buffers as described by product manual. The transfected cells are seeded directly onto a well of a 6-well plate coated with Matrigel containing cord blood culture medium supplemented with 4 ng/mL bFGF and 5 µg/mL fibronectin (BD Biosciences) without antibiotics. Cord blood culture medium consists of SFMII+CC110 (Stem Cell Technologies). Twenty-four hours post transfection, FRM is added to the culture in equal volume. The culture medium is switched entirely to FRM on day 5 with hygromycin removed 7 days post transfection. All reprogramming cultures are switched to FMM 14 days post transfection. Twenty-four hours post transfection, FRM is added in equal volume and continuously added every few days until day 14 post transfection when the culture is aspirated and replaced with entirely FMM. Clusters of adherent rounded cells are seen around 5 to 7 days post transfection. Once in FMM, all reprogramming cultures are maintained and single cell passaged using Accutase on Matrigel coated surfaces (described above). The single cell dissociated cells are expanded onto Matrigel coated plates with FMM and maintained until flow cytometry sorting.

Example 5

Real-Time RT-PCR and Fluidigm Analysis

Total RNA of the cells according to Example 2 was isolated using Pico Pure RNA Isolation Kit (Life Technologies). Complimentary DNA (cDNA) was reverse transcribed from 100 ng of isolated total RNA using the iScript cDNA Synthesis Kit (Bio-Rad). The cDNA was then used for pre-amplification of specific target genes and two reference control genes using the TaqMan PreAmp Master Mix Kit (Life Technologies) and a 0.2× concentration of pooled TaqMan assays. Specific target amplification (STA) from cDNA was performed using 14 cycles of amplification with the standard cycling conditions stated in the manufacturer's protocol. The pre-amplified cDNA reactions (n=48) were diluted 1:5 (in sterile water) and used as template for the real-time quantitative PCR reactions. 48.48 Dynamic arrays (Fluidigm) were loaded using a NanoFlex IFC Controller MX (Fluidigm) with TaqMan assays loaded in duplicate and real-time reactions were performed using a BioMark Real-Time PCR System (Fluidigm). Results were analyzed using BioMark Real-Time PCR Analysis software (Fluidigm). Samples with cycle thresholds (Cts) above 32 were excluded from the calculations. In case of hESC control analysis, assay replicates were used to determine SEM. Average Cts were calculated using the mean of two reference genes (GAPDH and HPRT1) against the median of six control MEF cell lines (OSK hiPSCs on MEF and H1 ESCs). Relative gene expression results are displayed in Excel (Microsoft) in heat map format. Cells cultured in FMM demonstrated a ground pluripotent as shown by a decreased expression of mesodermal, ectodermal and endodermal cell surface markers (see FIGS. 6A-6C).

TABLE 3

FAM-Labeled TaqMan Probes

| Assay ID | Catalog Number (Life Technologies) | Gene Symbol | RefSeq |
|---|---|---|---|
| Hs00232764_m1 | 4331182 | FOXA2 | NM_021784.4; NM_153675.2 |
| Hs00173490_m1 | 4331182 | AFP | NM_001134.1 |
| Hs00171403_m1 | 4331182 | GATA4 | NM_002052.3 |
| Hs00751752_s1 | 4331182 | SOX17 | NM_022454.3 |
| Hs00610080_m1 | 4331182 | T | NM_003181.2 |
| Hs00607978_s1 | 4331182 | CXCR4 | NM_003467.2; NM_001008540.1 |
| Hs00415443_m1 | 4331182 | NODAL | NM_018055.4 |
| Hs02330075_g1 | 4331182 | MYOD1 | NM_002478.4 |
| Hs00240871_m1 | 4331182 | PAX6 | NM_001127612.1 |
| Hs00801390_s1 | 4331182 | TUBB3 | NM_001197181.1; NM_006086.3 |
| Hs00374280_m1 | 4331182 | STAT3 | NM_139276.2; NM_213662.1; NM_003150.3 |
| Hs04260366_g1 | 4331182 | NANOG | NM_024865.2 |
| Hs00602736_s1 | 4331182 | SOX2 | NM_003106.3 |
| Hs00399279_m1 | 4331182 | ZFP42 | NM_174900.3 |
| Hs01003405_m1 | 4331182 | DNMT3B | NM_001207055.1; NM_001207056.1; NM_006892.3; NM_175848.1; NM_175850.2; NM_175849.1 |
| Hs00702808_s1 | 4331182 | LIN28A | NM_024674.4 |
| Hs99999003_m1 | 4331182 | MYC | NM_002467.4 |

TABLE 3-continued

| | | | |
|---|---|---|---|
| Hs01081364_m1 | 4331182 | DNMT3L | NM_013369.2; NM_175867.1 |
| Hs00360439_g1 | 4331182 | KLF2 | NM_016270.2 |
| Hs00222238_m1 | 4331182 | OTX2 | NM_172337.1; NM_021728.2 |
| Hs00242962_m1 | 4331182 | PAX7 | NM_001135254.1; NM_002584.2; NM_013945.2 |
| Hs00414521_g1 | 4331182 | DPPA2 | NM_138815.3 |
| Hs00216968_m1 | 4331182 | DPPA4 | NM_018189.3 |
| Hs99999905_m1 | 4331182 | GAPDH | NM_002046.4 |
| Hs01003267_m1 | 4331182 | HPRT1 | NM_000194.2 |

Custom-made TaqMan Gene Expression Assays

| Gene | Forward Primer | Reverse Primer |
|---|---|---|
| OCT4 | GGGTTTTTGG GATTAAGTTC TTCA (SEQ ID NO: 1) | GCCCCCACC CTTTGTGTT (SEQ ID NO: 2) |
| KLF4 | AGCCTAAATG ATGGTGCTTG GT (SEQ ID NO: 3) | TTGAAAACTT TGGCTTCCTT GTT (SEQ ID NO: 4) |

Example 6

Testing Presence of Transgenes

Genomic DNA of cells according to Example 2 was isolated using QIaamp® DNA Mini Kit and Proteinase K digestion (Qiagen). 100 ng of the genomic DNA was amplified using transgene-specific primer sets (Table 2 below) (Yu et al., 2007) using Taq PCR Master Mix Kit (Qiagen). The PCR reactions were run for 35 cycles as follows: 94° C. for 30 sec (denaturation), 60-64° C. for 30 sec (annealing) and 72° C. for 1 min (extension). Genomic DNA from fibroblasts and hiPSCs generated using lentiviral methods were used as negative controls. DNA of the episomal constructs was used as positive control (FIG. 4D).

TABLE 4

Transgene specific primer sets

| Amplified region | Forward | Reverse |
|---|---|---|
| Oct4-Oct4 region of episomal transgene | CAGGCCCGAA AGAGAAAGCG (SEQ ID NO: 5) | GGAGGGCCTT GGAAGCTTAG (SEQ ID NO: 6) |
| Oct4-NANOG region of episomal transgene | TATACACAGG CCGATGTGGG (SEQ ID NO: 7) | TTGACCGGGA CCTTGTCTTC (SEQ ID NO: 8) |
| OCT4-SOX2 region of episomal transgene | GTGGTCCGAG TGTGGTTCTG (SEQ ID NO: 9) | GTTCTCCTGG GCCATCTTGC (SEQ ID NO: 10) |
| Lin28-SV40pA episomal transgene | AAGCGCAGAT CAAAAGGAGA (SEQ ID NO: 11) | CCCCCTGAAC CTGAAACATA (SEQ ID NO: 12) |

TABLE 4-continued

Transgene specific primer sets

| Amplified region | Forward | Reverse |
|---|---|---|
| WPRE lentiviral element | TGCTTCCCGT ATGGCTTTC (SEQ ID NO: 13) | AAAGGGAGAT CCGACTCGTC TG (SEQ ID NO: 14) |
| EBNA1 | ATCGTCAAAG CTGCACACAG (SEQ ID NO: 15) | CCCAGGAGTC CCAGTAGTCA (SEQ ID NO: 16) |
| Human GAPDH | GTGGACCTGA CCTGCCGTCT (SEQ ID NO: 17) | GGAGGAGTGG GTGTCGCTGT (SEQ ID NO: 18) |

Example 7

Immunocytochemistry Analysis

Figure 5B:
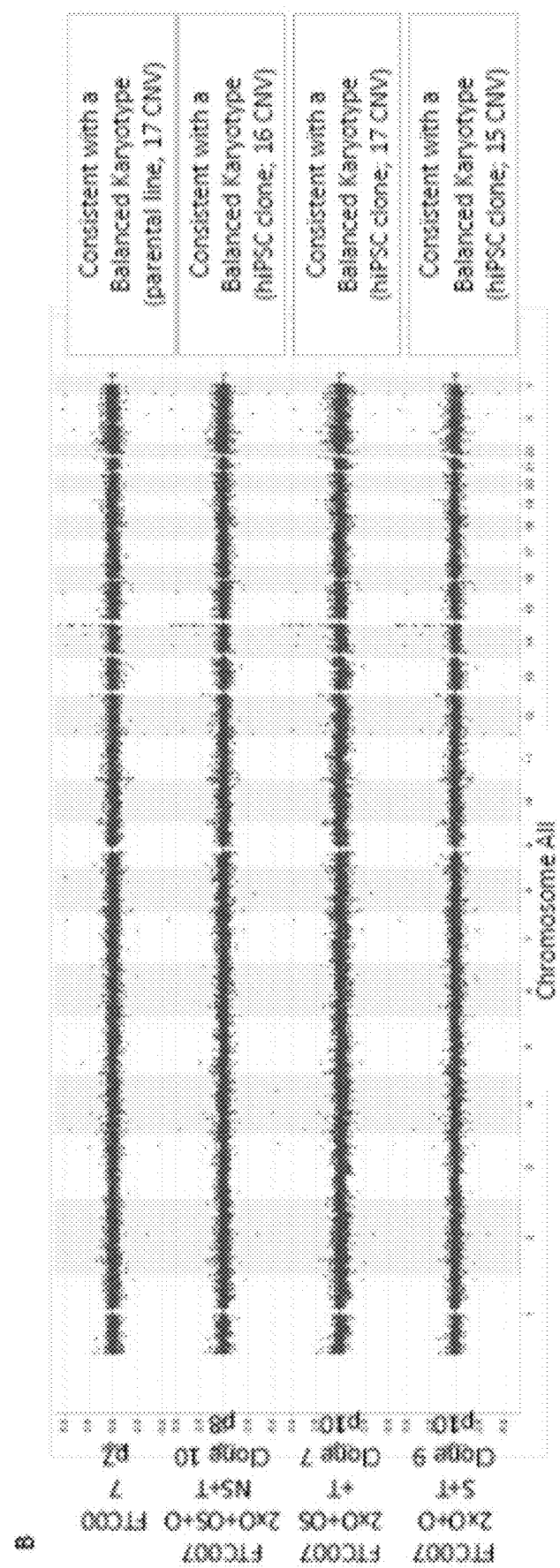
Figure 5C:
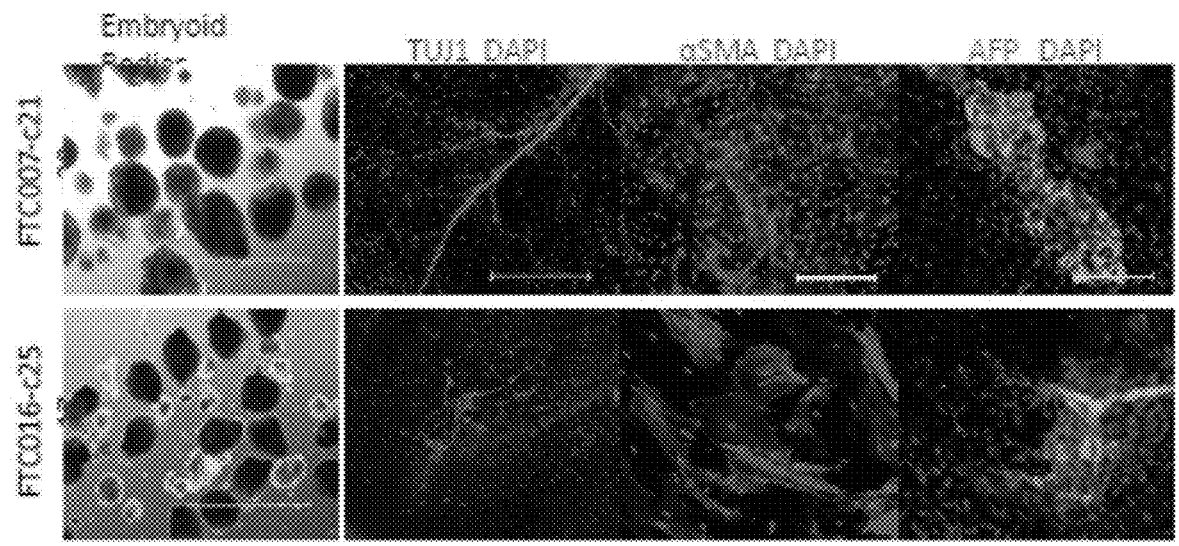
Figure 6A:
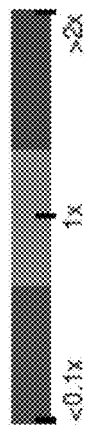
FIGS. 6A-6C. Generated hiPSCs resemble cells associated with the ground state of pluripotency.
Figure 6B:
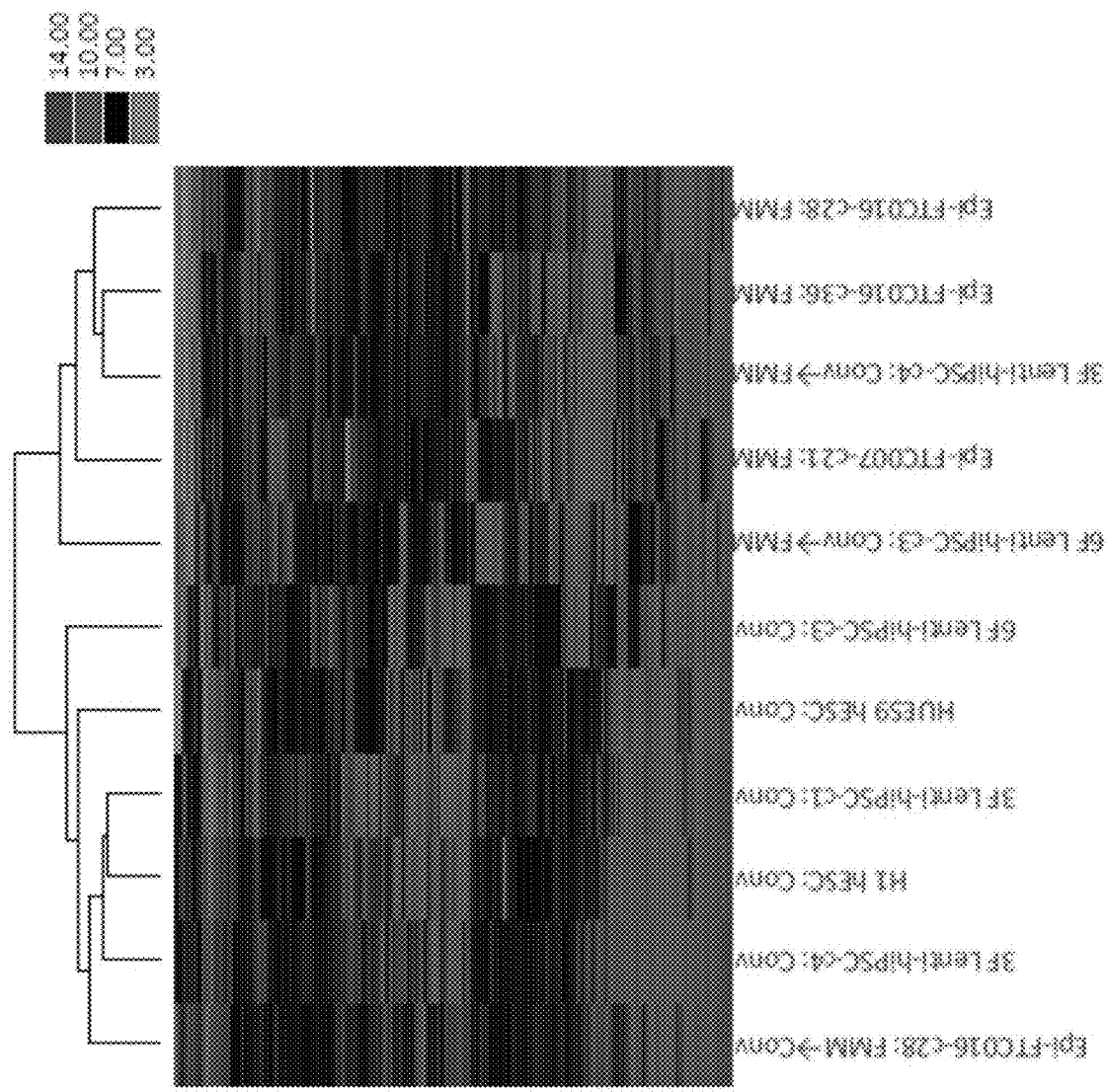
Figure 6C:
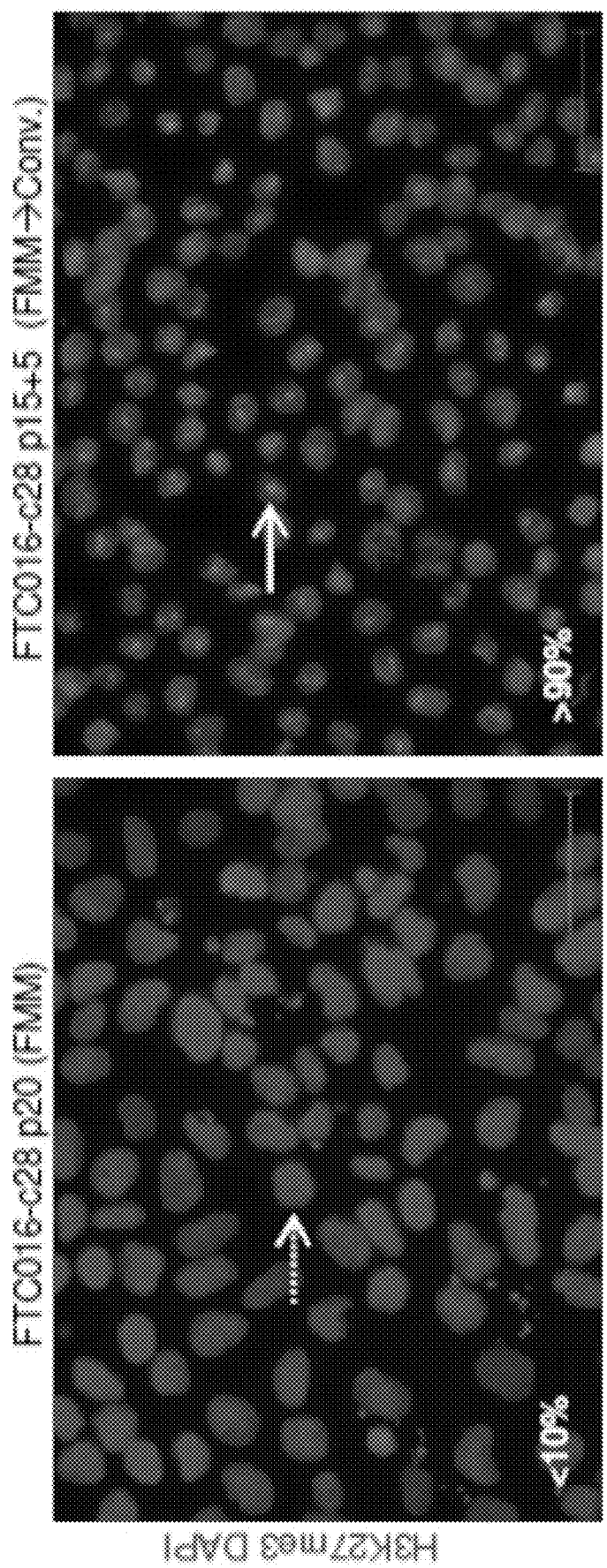

Cells according to Example 2 were fixed using 4% v/v paraformaldehyde (Alfa Aesar), washed three times with PBS containing 0.2% v/v Tween (PBST) (Fisher Scientific) and permeablized using 0.15% v/v TritonX-100 (Sigma-Aldrich) in PBS for 1 hr at 25° C. After permeabilization, cells were blocked with 1% v/v BSA (Sigma) in PBST (PBSTB) (Fisher Scientific) for 30 min at 25° C. After gentle removal of PBSTB, cells were incubated with primary antibody in PBSTB overnight at 4° C. Primary antibodies used in this study include OCT4 (Santa Cruz), NANOG (Santa Cruz), TRA160 (Millipore) and TRA181 (Millipore). β-III Tubulin (TUJ1, R&D Systems), α-Smooth Muscle Actin (Sigma), and Alpha-1-Fetoprotein (Dako) (FIG. 5C). After the overnight incubation, cells were washed three times with PBST and stained with secondary antibody (Alexa Fluor 488 or 555; Invitrogen) diluted 1:250 in PBSTB for 1 hr at 37° C. The cells were washed three times in PBST and stained with Hoechst dye (Invitrogen). For H3K27me3 staining analysis, hiPSCs were grown 72 to 96 hrs on cover slips and fixed with 4% parafomaldehyde (Electron Microscopy Science, EMS) in PBS for 15 min at 25° C. (FIG. 6C). Cell permeabilization was performed with 0.1% Triton X-100 in PBS for 1 hour at 25° C., and then cells were incubated with blocking solution (1% BSA in PBS) for 30 min at 25° C. After blocking, cover slips were incubated with 1:1600 dilution of anti-trimethyl-histone H3 (Lys27) antibody (Millipore 07-449, H3K27me3) in blocking solution, overnight at 4° C. Secondary antibodies were Alexa Fluor 555 Goat-anti-Rabbit IgG (Life Technologies, A21429). The nuclei were counterstained with DAPI and viewed with an Axio Observer Inverted Microscope (Carl Zeiss). Images were captured with the AxioVS40 v4.8.1.0 (Carl Zeiss Imaging Solutions Gmbh).

Example 8

Differentiation Analysis (EB and Directed)

hiPSC according to Example 2 were differentiated as EBs in differentiation medium containing DMEM/F12 (Mediatech), 20% fetal bovine serum (Invitrogen), 1% non-essential amino acids (Mediatech), 2 mM L-glutamine (Mediatech) and 100 μM β-mercaptoethanol. Briefly, for EB formation hiPSCs were seeded in FMM and switched to conventional medium the following day to prime the cells. After 3 to 4 days in conventional medium, cultures were single cell dissociated with Accutase (Millipore) and resuspended in differentiation medium including 10 μM Y27632 to a final concentration of 100,000 cells/mL. ROCK inhibitor Y27632 instead of Thiazovivn was used for EB formation. Cells were seeded at 100 μL/well in V-bottom 96-well non-tissue culture plate (Nunc) and centrifuged at 950 g for 5 min. The following day compact "ball-like clumps" were transferred to ultra-low binding 6-well plate (Corning) using P1000 at approximately 30-40 EBs/well in differentiation medium. After 7 days, EBs were transferred at 1:1 to Matrigel coated 6-well plate and fed with differentiation medium every three days. After 3 weeks in culture, cells were fixed and stained. For directed monolayer differentiation, hiPSCs were seeded on Matrigel coated wells in FMM to deliver 50% and 90% confluency the following day. Both densities were induced to differentiate. For neural induction (Lee et al., 2007), FMM media was replaced with hESC media supplemented with 10 μM SB431542 and 100 nM LDN-193189 (both SMAD inhibitors, Biovision). Following 2 days, differentiation media was supplemented with 3 μM CHIR99021 (Biovision) in addition to the dual SMAD inhibitors. Cells were fixed two days later and stained for Nestin (Abcam). For mesoderm differentiation, media was replaced with RPMI (Mediatech) supplemented with 1× B27 media additive (Life Technologies), 3 μM CHIR99021, 4 ng/ml bFGF and 10 ng/ml BMP4. Media was changed every other day and cells fixed on the 4th day and stained for αSMA (Sigma). Endoderm differentiation was performed using the Human Pluripotent Stem Cell Functional Identification Kit (R&D Systems). hiPSCs were incubated with endoderm differentiation media for 3 days, fixed and stained for SOX17 (R&D Systems). Cells demonstrated EB formation and stained positive for β-III Tubulin (TUJ1, R&D Systems), α-Smooth Muscle Actin (Sigma), and Alpha-1-Fetoprotein (Dako) (FIG. 5C).

Example 9

Gene Expression Analysis

RNA was extracted using the PicoPure RNA Isolation kit (Life Technologies) using the manufacturers recommended protocol. Total RNA was quantified using the Nanodrop 2000 Spectrophotometer (Thermo Scientific). In brief, biotinylated aRNA was prepared from roughly 100 ng of total RNA using the standard protocol for MessageAmp II aRNA Amplification Kit (Applied Biosystems/Ambion, Austin, Tex.) utilizing the optional Second Round Amplification and then transcribed into biotin labeled aRNA using MessageAmp II Biotin Enhanced Kit (Applied Biosystems/Ambion, Austin, Tex.) using the standard protocol. Biotin labeled aRNA was purified and fragmented according to Affymetrix recommendations. 20 μg of fragmented aRNA were used to hybridize to the Human Genome U133-plus-2.0 chips (Affymetrix Inc. Santa Clara, Calif.) for 16 hours at 45° C. The arrays were washed and stained in the Affymetrix Fluidics Station 450 and scanned using the Affymetrix GeneChip Scanner 3000 7G. Raw expression data files are available on Gene Expression Omnibus (GSE50868). The image data were analyzed using Affymetrix Expression Console software using default analysis settings. Arrays were normalized by log scale robust multi-array analysis (RMA, Affymetrix) and visualized in Spotfire for Genomics 4.5 (Tibco Spotfire, Palo Alto, Calif.). Biological pathway enrichment analysis of the differentially expressed probes was performed against the Gene Ontology (GO) database (Singular Enrichment to GO Biological Process and p-value <0.01) using Database for Annotation, Visualization and Integrated Discovery (DAVID v6.7) (Huang da et al., 2009a, b). Hierarchical clustering was performed to compare the gene expression profiles between samples based on Log 2 expression levels using a complete linkage clustering method with Euclidean distance measurements (Spotfire for Genomics 4.5). Probe sets for clustering were selected by either an overall differential in expression levels (> or <2.5-fold) or presence on targeted gene lists defining a ground or metastable state. For X Chromosome gene expression comparison, RMA normalized Affymetrix gene chip probe set intensities were converted to linear expression values by taking the $2^{\wedge}[RMA\ log\ 2\ intensity]$. Linear expression ratios were calculated as the naïve expression set divided by the primed expression set. The expression ratios for all 1688 probe sets mapped to the X chromosome were visualized in Spotfire 4.5 with the probe sets greater or less than 2 fold enrichment ratio highlighted (FIGS. 6A and 6B).

Example 10

Microarray (aCGH+SNP) Analysis

High resolution array comparative genomic hybridization+single nucleotide polymorphism (Agilent SurePrint G3 Human Genome CGH+SNP Microarray Kit, 4×180K; NCBI Build 37/hg19) and subsequent copy number variation and loss of heterozygosity analysis was conducted by WiCell Cytogenetics (Madison, Wis.). Relative copy number and regions of homozygosity was determined by comparative differential hybridization of labeled genomic DNA to the 180,000 oligonucleotide whole genome tiling array (FIG. 4B).

Example 11

Karyotype Analysis

Cytogenetic analysis was performed on G-banded metaphase cells by WiCell Research Institute (Madison, Wis.). Each karyotype analysis includes a minimum count of 20 spreads with analyses expanded to 40 spread counts when nonclonal aberrations are identified in the first 20 (FIGS. 5A and 5B).

Example 12

Teratoma Formation

Figure 5D:
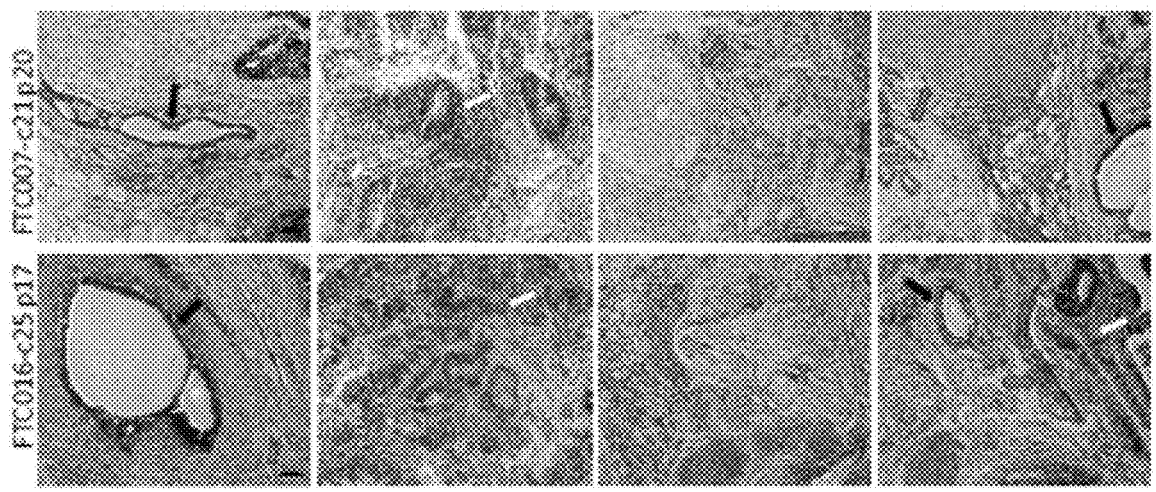

Single cell dissociated hiPSCs, at concentrations of 0.5 and 3 million cells per 200 solution (100 μL FMM and 100 μL Matrigel) were injected subcutaneously into NOD/SCID/$\gamma^{null}$ mice. After 5-6 weeks (3 million cells injection) and 7-8 weeks (0.5 million cells injection), teratomas were harvested in PBS, fixed overnight at room temperature in 4% paraformaldehyde and maintained thereafter in 70% ethanol at room temperature for processing. Samples were sectioned and stained with hematoxylin and eosin. Sections were examined, interpreted and photographed using a Nikon Eclipse TS100 microscope equipped with a Nikon DS-Fi1 camera (FIG. 5D).

Example 13

Conclusions

The above experiments demonstrate that segments of umbilical cord blood banks (or peripheral blood) can be reproducibly reprogrammed in fully defined culture media to derive hiPSC cell culture banks having pre-characterized HLA types. This strategy provides access to unique HLA type cord blood units without comprising the banked cord and represents a cost effective strategy to generate allogeneic hiPSC-derived therapeutic cells prepared in advance of therapeutic need. The reprogramming methodologies disclosed herein significantly enhance reprogramming kinetics of non-integrative induction systems, delivering a consistent and reproducible derivation method without the need for oncogenes such as KLF4 or c-MYC. Expansion of single cell sorted hiPSCs in FMM ensures clonality, pluripotency and genomic integrity of each hiPSC line. hiPSCs generated from UCB using the methodologies disclosed herein can be banked under cGMP conditions to provide an attractive source of cells for downstream differentiated cell therapy applications.

The invention claimed is:

1. A composition comprising CD34+ mononuclear cells, wherein the CD34+ mononuclear cells:
    (a) are from an individual segment of umbilical cord blood (UCB) comprising at least $1 \times 10^3$ mononuclear cells, wherein the individual segment has a volume of less than 500 uL; and
    (b) comprise:
        (i) at least one exogenous nonintegrated polynucleotide encoding one or more of octamer-binding transcription factor 4 (OCT4), sex determining region Y box 2 (SOX2) and Simian virus 40 large antigen (SV4OLT); or one or more exogenous polypeptides selected from the group consisting of an OCT4 polypeptide, a SOX2 polypeptide, and an SV4OLT polypeptide; and
        (ii) CD45+/CD34+/Lineage− cells; and
    wherein the CD34+ mononuclear cells are suitable for being reprogrammed into induced pluripotent stem cells (iPSCs) without increasing the volume of the individual segment to more than 500 uL and wherein the reprogrammed iPSCs co-express SSEA4 and TRA181 with reprogramming efficiency of at least 0.1% efficiency based on the number of iPSCs divided by the number of CD34+ mononuclear cells in the individual segment.

2. The composition of claim 1, wherein the individual sample comprises about $1 \times 10^3$ to about $1 \times 10^6$ mononuclear cells.

3. The composition of claim 1, wherein the individual segment of UCB is an individual sample of cryopreserved UCB.

4. The composition of claim 1, wherein the reprogramming efficiency is at least 1%.

5. The composition of claim 1, wherein the CD34+ mononuclear cells comprise the at least one exogenous polynucleotide, and wherein the at least one exogenous polynucleotide is not integrated into the genomes of the mononuclear cells.

6. The composition of claim 1, wherein the CD34+ mononuclear cells comprise the at least one exogenous polynucleotide, and wherein the at least one exogenous polynucleotide is selected from the group consisting of a non-integrating lentivirus, an episome, mRNA, Sendai virus, miRNA, and self-replicating RNA.

7. The composition of claim 1, wherein the composition is free of exogenous polynucleotides encoding Avian Myelocytomatosis Viral Oncogene Homolog (c-MYC) and Kruppel-like factor 4 (KLF4) and is free of exogenous c-MYC and KLF4 polypeptides.

8. The composition of claim 1, wherein the CD34+ mononuclear cells comprise expanded or unexpanded CD45+/CD34+/Lineage− progenitor cells.

9. The composition of claim 1, further comprising at least one inhibitor selected from the group consisting of: a glycogen synthase kinase 3 (GSK3) inhibitor, a mitogen-activated protein kinase kinase enzyme (MEK) inhibitor, a rho-associated protein kinase (ROCK) inhibitor, and a transforming growth factor β receptor (TGFβR) inhibitor.

10. The composition of claim 1, wherein the composition
    (i) is free of feeder cells, or
    (ii) comprises a defined culture medium.

11. The composition of claim 1, wherein the CD34+ mononuclear cells comprise hematopoietic stem or progenitor cells.

12. The composition of claim 11, wherein the hematopoietic stem or progenitor cells are suitable for hematopoietic reconstitution in a subject in need of cell therapy.

13. The composition of claim 1, wherein the CD34+ mononuclear cells are
    (i) allogeneic to a subject in need of cell therapy, and
    (ii) HLA matched to the subject.

14. The composition of claim 1, wherein the individual sample has a volume of about 50 μL to about 500 μL.

15. The composition of claim 1, wherein the individual sample has a volume selected from the group consisting of: less than 400 μL, less than 300 μL, less than 200 μL, less than 100 μL, less than 50 μL, less than 25 μL, and less than 10 μL.

* * * * *

SEQUENCE LISTING

<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Forward Primer for OCT4 TaqMan Gene Expression
      Assay

<400> SEQUENCE: 1
gggtttttgg gattaagttc ttca                                           24

<210> SEQ ID NO 2
<211> LENGTH: 18
<212> TYPE: DNA
<213> ORGANISM: Artificial Sequence
<220> FEATURE:
<223> OTHER INFORMATION: Reverse Primer for OCT4 TaqMan Gene Expression
      Assay

<400> SEQUENCE: 2
gcccccaccc tttgtgtt                                                  18

<210> SEQ ID NO 3
<211> LENGTH: 22
<212> TYPE: DNA
<213> ORGANISM: Artificial Sequence
<220> FEATURE:
<223> OTHER INFORMATION: Forward Primer for KLF4 TaqMan Gene Expression
      Assay

<400> SEQUENCE: 3
agcctaaatg atggtgcttg gt                                             22

<210> SEQ ID NO 4
<211> LENGTH: 23
<212> TYPE: DNA
<213> ORGANISM: Artificial Sequence
<220> FEATURE:
<223> OTHER INFORMATION: Reverse Primer for KLF4 TaqMan Gene Expression
      Assay

<400> SEQUENCE: 4
ttgaaaactt tggcttcctt gtt                                            23

<210> SEQ ID NO 5
<211> LENGTH: 20
<212> TYPE: DNA
<213> ORGANISM: Artificial Sequence
<220> FEATURE:
<223> OTHER INFORMATION: Forward Primer for amplifying Oct4-Oct4 region
      of episomal transgene

<400> SEQUENCE: 5
caggcccgaa agagaaagcg                                                20

```
<210> SEQ ID NO 6
<211> LENGTH: 20
<212> TYPE: DNA
<213> ORGANISM: Artificial Sequence
<220> FEATURE:
<223> OTHER INFORMATION: Reverse Primer for amplifying Oct4-Oct4 region
      of episomal transgene

<400> SEQUENCE: 6
ggagggcctt ggaagcttag                                                    20

<210> SEQ ID NO 7
<211> LENGTH: 20
<212> TYPE: DNA
<213> ORGANISM: Artificial Sequence
<220> FEATURE:
<223> OTHER INFORMATION: Forward Primer for amplifying Oct4-NANOG region
      of episomal transgene

<400> SEQUENCE: 7
tatacacagg ccgatgtggg                                                    20

<210> SEQ ID NO 8
<211> LENGTH: 20
<212> TYPE: DNA
<213> ORGANISM: Artificial Sequence
<220> FEATURE:
<223> OTHER INFORMATION: Reverse Primer for amplifying Oct4-NANOG region
      of episomal transgene

<400> SEQUENCE: 8
ttgaccggga ccttgtcttc                                                    20

<210> SEQ ID NO 9
<211> LENGTH: 20
<212> TYPE: DNA
<213> ORGANISM: Artificial Sequence
<220> FEATURE:
<223> OTHER INFORMATION: Forward Primer for amplifying Oct4-SOX2 region
      of episomal transgene

<400> SEQUENCE: 9
gtggtccgag tgtggttctg                                                    20

<210> SEQ ID NO 10
<211> LENGTH: 20
<212> TYPE: DNA
<213> ORGANISM: Artificial Sequence
<220> FEATURE:
<223> OTHER INFORMATION: Reverse Primer for amplifying Oct4-SOX2 region
      of episomal transgene

<400> SEQUENCE: 10
gttctcctgg gccatcttgc                                                    20

<210> SEQ ID NO 11
<211> LENGTH: 20
<212> TYPE: DNA
<213> ORGANISM: Artificial Sequence
<220> FEATURE:
<223> OTHER INFORMATION: Forward Primer for amplifying Lin28-SV40pA
      episomal transgene

<400> SEQUENCE: 11
aagcgcagat caaaaggaga                                                    20
```

```
<210> SEQ ID NO 12
<211> LENGTH: 20
<212> TYPE: DNA
<213> ORGANISM: Artificial Sequence
<220> FEATURE:
<223> OTHER INFORMATION: Reverse Primer for amplifying Lin28-SV40pA
      episomal transgene

<400> SEQUENCE: 12 cccccctgaac ctgaaacata                                              20

<210> SEQ ID NO 13
<211> LENGTH: 19
<212> TYPE: DNA
<213> ORGANISM: Artificial Sequence
<220> FEATURE:
<223> OTHER INFORMATION: Forward Primer for amplifying WPRE lentiviral
      element

<400> SEQUENCE: 13
tgcttcccgt atggctttc                                                19

<210> SEQ ID NO 14
<211> LENGTH: 22
<212> TYPE: DNA
<213> ORGANISM: Artificial Sequence
<220> FEATURE:
<223> OTHER INFORMATION: Reverse Primer for amplifying WPRE lentiviral
      element

<400> SEQUENCE: 14
aaagggagat ccgactcgtc tg                                            22

<210> SEQ ID NO 15
<211> LENGTH: 20
<212> TYPE: DNA
<213> ORGANISM: Artificial Sequence
<220> FEATURE:
<223> OTHER INFORMATION: Forward Primer for amplifying EBNA1

<400> SEQUENCE: 15
atcgtcaaag ctgcacacag                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse Primer for amplifying EBNA1

<400> SEQUENCE: 16
cccaggagtc ccagtagtca                                               20

<210> SEQ ID NO 17
<211> LENGTH: 20
<212> TYPE: DNA
<213> ORGANISM: Artificial Sequence
<220> FEATURE:
<223> OTHER INFORMATION: Forward Primer for amplifying Human GAPDH

<400> SEQUENCE: 17
gtggacctga cctgccgtct                                               20

<210> SEQ ID NO 18
<211> LENGTH: 20
<212> TYPE: DNA
<213> ORGANISM: Artificial Sequence
```

```
<220> FEATURE:
<223> OTHER INFORMATION: Reverse Primer for amplifying Human GAPDH

<400> SEQUENCE: 18
ggaggagtgg gtgtcgctgt                                              20
```